(12) United States Patent
Galili

(10) Patent No.: US 9,072,795 B2
(45) Date of Patent: *Jul. 7, 2015

(54) COMPOSITIONS AND METHODS FOR WOUND HEALING

(75) Inventor: Uri Galili, Shrewsbury, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 690 days.

This patent is subject to a terminal disclaimer.

(21) Appl. No.: 13/253,601

(22) Filed: Oct. 5, 2011

(65) Prior Publication Data

US 2012/0045503 A1 Feb. 23, 2012

Related U.S. Application Data

(60) Division of application No. 12/542,377, filed on Aug. 17, 2009, now Pat. No. 8,084,057, which is a continuation-in-part of application No. PCT/US2008/008731, filed on Jul. 17, 2008, now abandoned.

(60) Provisional application No. 60/961,047, filed on Jul. 17, 2007.

(51) Int. Cl.
*A61K 39/395* (2006.01)
*A61K 9/127* (2006.01)
*A61K 35/28* (2006.01)
*A61K 47/48* (2006.01)
*A61K 9/00* (2006.01)

(52) U.S. Cl.
CPC ......... *A61K 47/48815* (2013.01); *A61K 9/0014* (2013.01); *A61K 9/0019* (2013.01)

(58) Field of Classification Search
None
See application file for complete search history.

(56) References Cited

U.S. PATENT DOCUMENTS

| 5,705,188 | A | 1/1998 | Junichi et al. |
| 2004/0043006 | A1 | 3/2004 | Badylak et al. |
| 2004/0234507 | A1 | 11/2004 | Stone |
| 2005/0112118 | A1 | 5/2005 | Cimbora et al. |
| 2005/0112141 | A1 | 5/2005 | Terman |
| 2006/0258562 | A1 | 11/2006 | Tennenbaum |

FOREIGN PATENT DOCUMENTS

WO    WO 97/30731    8/1997

OTHER PUBLICATIONS

U.S. Appl. No. 60/961,047, filed Jul. 17, 2007, Galili.
Aderem and Underhill, "Mechanisms of Phagocytosis in Macrophages." *Annu Rev Immunol*, 17:593-623 (1999).
Bryant, et al., "Mediation of Post-Surgical Wound Healing by Macrophages." *Prog Clin Biol Res*, 266:273-290 (1988).
Clark, "Basics of Cutaneous Wound Repair." *J Dermatol Surg Oncol*, 19(8):693-706 (1993).
Collins, et al., "Cardiac Xenografts between Primate Species Provide Evidence for the Importance of the Alpha-Galactosyl Determinant in Hyperacute Rejection." *J Immunol*, 154(10):5500-5510 (1995).
Dabrowski, et al., "Immunochemistry of I/I-Active Oligo- and Polyglycosylceramides from Rabbit Erythrocyte Membranes. Determination of Branching Patterns of a Ceramide Pentadecasaccharide by 1H Nuclear Magnetic Resonance." *J Biol Chem*, 259(12):7648-7651 (1984).
Danon, et al., "Treatment of Human Ulcers by Application of Macrophages Prepared from a Blood Unit." *Exp Gerontol*, 32(6):633-641 (1997).
Dinarello, "Biology of Interleukin 1." *FASEB J*, 2(2):108-115 (1988).
DiPietro, "Wound Healing: The Role of the Macrophage and Other Immune Cells." *Shock*, 4(4):233-240 (1995).
Eisenberg, et al., "Bone Marrow Cells Transdifferentiate to Cardiomyocytes When Introduced into the Embryonic Heart." *Stem Cells*, 24(5):1236-1245 (2006).
Eto, et al., "Chemistry of Lipid of the Posthemyolytic Residue or Stroma of Erythrocytes. XVI. Occurrence of Ceramide Pentasaccharide in the Membrane of Erythrocytes and Reticulocytes of Rabbit." *J Biochem*, 64(2):205-213 (1968).
Frangogiannis, "Targeting the Inflammatory Response in Healing Myocardial Infarcts." *Curr Med Chem*, 13(16):1877-1893 (2006).
Galili, et al., "A Unique Natural Human IgG Antibody with Anti-α-Galactosyl Specificity." *J Exp Med*, 160(5):1519-1531 (1984).
Galili, et al., "Identification of Erythrocyte Galα1-3Gal Glycosphingolipids with a Mouse Monoclonal Antibody, Gal-13." *J Biol Chem*, 262(10):4683-4688 (1987a).
Galili, et al., "Interaction between Human Natural Anti-α-Galactosyl Immunoglobulin G and Bacteria of the Human Flora." *Infect Immun*, 56(7):1730-1737 (1988a).
Galili, et al., "Man, Apes, and Old World Monkeys Differ from Other Mammals in the Expression of α-Galactosyl Epitopes on Nucleated Cells." *J Biol Chem*, 263(33):17755-17762 (1988b).
Galili, "Evolution and Pathophysiology of the Human Natural Anti-α-Galactosyl IgG(Anti-Gal) Antibody." *Springer Seminars in Immunopathology*, 15(2-3):155-171 (1993a).
Galili, "Interaction of the Natural Anti-Gal Antibody with α-Galactosyl Epitopes: A Major Obstacle for Xenotransplantation in Humans." *Immunol Today*, 14(10):480-482 (1993b).
Galili, et al., "A Sensitive Assay for Measuring α-Gal Epitope Expression on Cells by a Monoclonal Anti-Gal Antibody." *Transplantation*, 65(8):1129-1132 (1998).

(Continued)

*Primary Examiner* — Michail Belyavskyi
(74) *Attorney, Agent, or Firm* — Medlen & Carroll, LLP

(57) ABSTRACT

The present invention is related to the field of wound healing or tissue regeneration due to disease (i.e., for example, cardiovascular diseases, osteoarthritic diseases, or diabetes). In particular, the present invention provides compositions and methods comprising molecules with linked α-gal epitopes for induction of recruitment of macrophages localized within or surrounding damaged tissue. The recruited macrophages and stem cells promote the repair and regeneration of the treated injured tissue. In some embodiments, the present invention provides treatments for tissue repair in normal subjects and in subjects having impaired healing capabilities, such as diabetic and aged subjects. In some embodiments, the present invention provides treatments for injured tissues such as brain, peripheral nerve, muscle, cartilage, bone, gastrointestinal tract and dysfunctional endocrine tissues.

9 Claims, 19 Drawing Sheets

(56) References Cited

OTHER PUBLICATIONS

Galili, "Autologous Tumor Vaccines Processed to α-Gal Epitopes: A Practical Approach to Immunotherapy in Cancer." *Cancer Immunology, Immunotherapy*, 53(11):935-945 (2004).

Hanfland, et al., "Structure Elucidation of Blood Group B-Like and I-Active Ceramide Eicosa- and Pentacosasaccharides from Rabbit Erythrocyte Membranes by Combined Gas Chromatography-Mass Spectrometry; Electron-Impact and Fast-Atom-Bombardment Mass Spectrometry; and Two-Dimensional Correlated, Relayed-Coherence Transfer, and Nuclear Overhauser Effect 500-MHz [1] H-N.M.R. Spectroscopy." *Carbohydr Res*, 178:1-21 (1988).

Honma, et al., "Isolation and Partial Structural Characterization of Macroglycolipid from Rabbit Erythrocyte Membranes." *J Biochem*, 90(4):1187-1196 (1981).

Knighton and Fiegel, "The Macrophages: Effector Cell Wound Repair." *Prog Clin Biol Res*, 299:217-226 (1989).

Leibovich and Ross, "The Role of the Macrophage in Wound Repair. A Study with Hydrocortisone and Antimacrophage Serum." *Am J Pathol*, 78(1):71-100 (1975).

Mateo, et al., "Interleukin-6 Activity in Wounds." *Am J Physiol*, 266(6 Pt 2):R1840-1844 (1994).

Nathan, "Secretory Products of Macrophages." *J Clin Invest*, 79(2):319-326 (1987).

Orenstein, et al., "Treatment of Deep Sternal Wound Infections Post-Open Heart Surgery by Application of Activated Macrophage Suspension." *Wound Repair Regen*, 13(3):237-242 (2005).

Ott, et al., "Inhalation of Carbon Monoxide Prevents Liver Injury and Inflammation Following Hind Limb Ischemia/Reperfusion." *FASEB J*, 19(1):106-108 (2005).

Rappolee and Werb, "Macrophage-Derived Growth Factors." *Curr Top Microbiol Immunol*, 181:87-140 (1992).

Sandrin, et al., "Natural Human Anti-Galα(1,3)Gal Antibodies React with Human Mucin Peptides." *Glycoconj J*, 14(1):97-105 (1997).

Schirmer, et al., "Effective Antiplatelet Therapy Does Not Prolong Transgenic Pig to Baboon Cardiac Xenograft Survival." *Xenotransplantation*, 11(5):436-443 (2004).

Schmid, et al., "The Disulfide Bonds of $\alpha_1$-Acid Glycoprotein." *Biochemistry*, 13(13):2694-2697 (1974).

Seta and Kuwana, "Human Circulating Monocytes as Multipotential Progenitors." *Keio J Med*, 56(2):41-47 (2007).

Singer and Clark, "Cutaneous Wound Healing." *N Engl J Med*, 341(10):738-746 (1999).

Stein and Keshav, "The Versatility of Macrophages." *Clinical & Experimental Allergy*, 22(1):19-27 (1992).

Stellner, et al., "Determination of Aminosugar Linkages in Glycolipids by Methylation. Aminosugar Linkages of Ceramide Pentasaccharides of Rabbit Erythrocytes and of Forssman Antigen." *Arch Biochem Biophys*, 155(2):464-472 (1973).

Stone, et al., "Replacement of Human Anterior Cruciate Ligaments with Pig Ligaments: A Model for Anti-Non-Gal Antibody Response in Long-Term Xenotransplantation." *Transplantation*, 83(2):211-219 (2007).

Tanemura, et al., "Differential Immune Responses to α-gal Epitopes on Xenografts and Allografts: Implications for Accommodation in Xenotransplantation." *J Clin Invest*, 105(3):301-310 (2000).

Thall, et al., "Oocyte Galα1,3Gal Epitopes Implicated in Sperm Adhesion to the Zona Pellucida Glycoprotein Zp3 Are Not Required for Fertilization in the Mouse." *J Biol Chem*, 270(37):21437-21440 (1995).

Wood, et al., "Immunochemical Studies of the Combining Sites of the Two Isolectins, A4 and B4, Isolated from *Bandeiraea simplicifolia*." *Arch Biochem Biophys*, 198(1):1-11 (1979).

Zhong, et al., "Improvement in Human Decay Accelerating Factor Transgenic Porcine Kidney Xenograft Rejection with Intravenous Administration of GAS914, a Polymeric Form of αgal." *Transplantation*, 75(1):10-19 (2003).

ISR PCT/US2008/008731.

Galili, et al. "Evolutionary Relationship between the Natural Anti-Gal Antibody and the Natural Anti-Gal Antibody and the Galα1→3Gal Epitope in Primates." *Proc Natl Acad Sci U S A* 84(5):1369-1373 (1987b).

Joziasse, et al. "α-1→3-Galactosyltransferase: The Use of Recombinant Enzyme for the Synthesis of Alpha-Galactosylated Glycoconjugates." *Eur J Biochem*, 191(1):75-83 (1990).

COMPOSITIONS AND METHODS FOR WOUND HEALING

This is a divisional application of, and claims priority to, U.S. patent application Ser. No. 12/542,377, filed on Aug. 17, 2009 now U.S. Pat. No. 8,084,057, which is a continuation-in-part of, and claims priority to, PCT application No. PCT/US2008/008731, filed on Jul. 17, 2008, now abandoned, which claims priority to U.S. provisional Patent Application Ser. No. 60/961,047, filed on Jul. 17, 2007, each of which is incorporated by reference.

FIELD OF INVENTION

The present invention is related to the field of wound healing. In particular, the present invention provides compositions and methods comprising molecules with linked α-gal epitopes for induction of an inflammatory response localized within or surrounding damaged tissue. In some embodiments, the present invention provides treatments for tissue repair and regeneration in normal subjects and in subjects having impaired healing capabilities, such as diabetic and aged subjects.

BACKGROUND OF THE INVENTION

The inflammatory phase plays a critical role in wound healing regardless of the cause of the tissue damage. In addition to the destroying invading microbes, the inflammatory process is an integral part of the tissue repair process. Neutrophils are the first immune cells to arrive at the wound site where they phagocytose microbial agents and mediate wound debridement. Macrophages migrate into the wound two to three days post injury and become the predominant cell population before fibroblast migration and replication takes place. Compositions and methods to accelerate the pace and/or extent of wound healing are desirable, particularly in individuals with impaired healing capabilities, such as diabetic and aged individuals. Thus, there is a need for methods and compositions that promote healing in both external and internal wounds.

SUMMARY OF THE INVENTION

The present invention is related to the field of wound healing. In particular, the present invention provides compositions and methods comprising molecules with linked α-gal epitopes for induction of an inflammatory response localized within or surrounding damaged tissue and promotion of healing and repair of the injured tissue. In some embodiments, the present invention provides treatments for tissue repair in normal subjects and in subjects having impaired healing capabilities, such as diabetic and aged subjects.

In one embodiment, the present invention contemplates a method, comprising: a) providing; i) a subject having endogenous anti-Gal antibody, wherein the subject has an injured tissue; and ii) a preparation comprising an α-gal epitope having a terminal α-galactosyl; and b) applying said preparation to said tissue under conditions such that healing of said injured tissue is accelerated. In one embodiment, the tissue is an internal tissue. In one embodiment, the terminal α-galactosyl is selected from the group consisting of Galα1-3Gal, Galα1-2Gal, Galα1-6Gal, α-galactose sugar units capable of binding anti-Gal antibodies and α-gal epitope mimicking peptides linked to a macromolecule backbone or to another linker and they are capable of binding the anti-Gal antibody. In one embodiment, the α-gal epitope is soluble. In one embodiment, the α-gal epitope is attached to a molecule selected from the group consisting of a natural or synthetic glycolipid, glycoprotein, proteoglycan and a glycopolymer. In one embodiment, the preparation comprises α-gal liposomes. In one embodiment, the α-gal liposomes further comprise anti-Gal antibodies.

In one embodiment, the preparation further comprises an injury care device selected from the group consisting of syringes, adhesive bands, compression bandages, sponges, gels, semi-permeable films, plasma clots, fibrin clots. In one embodiment, the device comprises physiological compositions including, but not limited to, solutions, suspensions, emulsions, creams, ointments, aerosol sprays, collagen containing substances, stabilizers, drops, matrix-forming substances, foams and/or dried preparation. In one embodiment, the preparation further comprises anti-Gal antibodies bound to said α-gal liposomes. In one embodiment, the injured internal tissue is selected from the group consisting of skin tissue brain tissue, nerve tissue, eye tissue, gastrointestinal tissue, muscle tissue, heart tissue, cartilage tissue, bone tissue, connective tissue, endocrine glands and/or vascular tissue. In one embodiment, the preparation comprises α-gal liposomes.

In one embodiment, the present invention contemplates a method, comprising: a) providing; i) a diabetic subject having endogenous anti-Gal antibody, wherein said subject has an injured pancreas such that insulin production is impaired; and ii) a preparation comprising an α-gal epitope having a terminal α-galactosyl; and b) applying said preparation to said pancreas, thereby creating regenerated Langerhans Islet cells. In one embodiment, the terminal α-galactosyl is selected from the group consisting of Galα1-3Gal, Galα1-2Gal, Galα1-6Gal, and α-galactose sugar units capable of binding anti-Gal antibodies. In one embodiment, the α-gal epitope is soluble. In one embodiment, the α-gal epitope is bound to a molecule selected from the group consisting of a natural or synthetic glycolipid, glycoprotein, and a glycopolymer. In one embodiment, the preparation comprises α-gal epitope mimicking peptides linked to a macromolecule backbone or to another linker and they are capable of binding the anti-Gal antibody. In one embodiment, the preparation further comprises α-gal liposomes. In one embodiment, the α-gal liposomes further comprise anti-Gal antibodies bound to α-gal liposomes. In one embodiment, the preparation further comprises an injury care device selected from the group consisting of syringes, adhesive bands, compression bandages, sponges, gels, semi-permeable films, plasma clots, fibrin clots. In one embodiment, the device comprises physiological compositions including, but not limited to, solutions, suspensions, emulsions, creams, ointments, aerosol sprays, collagen containing substances, stabilizers, drops, matrix-forming substances, foams and/or dried preparation. In one embodiment, the regenerated Langerhans Islet cells produce insulin.

In one embodiment, the present invention contemplates a method, comprising: a) providing; i) a subject having endogenous anti-Gal antibody and having an injured tissue selected from the group consisting of a peripheral nerve, a spinal cord, and a blood vessel. ii) a device comprising a biodegradable or non-biodegradable sheet comprising a preparation comprising an α-gal epitope having a terminal α-galactosyl; and b) wrapping said sheet around said injured tissue under conditions such that regeneration of said injured tissue is accelerated. In one embodiment, the terminal α-galactosyl is selected from the group consisting of Galα1-3Gal, Galα1-2Gal, Galα1-6Gal and any α-galactose sugar units capable of binding anti-Gal antibodies. In one embodiment, the α-gal epitope is soluble. In one embodiment, the α-gal epitope is bound to a molecule selected from the group consisting of a natural or synthetic glycolipid, glycoprotein, and a glycopolymer. In one embodiment, the preparation comprises α-gal epitope mimicking peptides linked to a macromolecule backbone or to another linker and they are capable of binding the anti-Gal antibody. In one embodiment, the preparation comprises α-gal liposomes. In one embodiment, the preparation further comprises anti-Gal antibodies bound to said α-gal liposomes. In one embodiment, the sheet is selected from the group consisting of a collagen sheet and a synthetic sheet.

In one embodiment, the present invention contemplates a method, comprising: a) providing: i) a subject having endogenous anti-Gal antibody; ii) damaged brain tissue; and iii) a preparation comprising an α-gal epitope having a terminal galactosyl; b) applying said preparation to said damaged brain tissue to produce treated brain tissue. In further embodiments, said terminal α-galactosyl is selected from the group consisting of Galα1-3Gal and Galα1-6Gal. In still further embodiments, said α-gal epitope is part of a molecule selected from the group consisting of a glycolipid, a glycoprotein, proteoglycan and a glycopolymer. In some embodiments, the preparation comprises α-gal epitope mimicking peptides linked to a macromolecule backbone or to another linker and they are capable of binding the anti-Gal antibody. In additional embodiments, said glycolipid comprises α-gal liposomes. In some embodiments, said applying is under conditions such that complement activation within or adjacent to said damaged tissue is enhanced. In further embodiments, said complement activation comprises production of C5a, C4a and C3a. In still further embodiments, said applying is under conditions such that neutrophil recruitment within or adjacent to said injured tissue is enhanced. In additional embodiments, said applying is under conditions such that monocyte and macrophage recruitment within or adjacent to said injured tissue is enhanced. In some embodiments, said applying is under conditions such that repair of said injured tissue is accelerated.

In one embodiment, the present invention contemplates a method, comprising: a) providing: i) a subject having endogenous anti-Gal antibody; ii) damaged skeletal muscle tissue; and iii) a preparation comprising an α-gal epitope having a terminal galactosyl; b) applying said preparation to said damaged skeletal muscle to produce treated skeletal muscle tissue. In further embodiments, said terminal α-galactosyl is selected from the group consisting of Galα1-3Gal and Galα1-6Gal. In still further embodiments, said α-gal epitope is part of a molecule selected from the group consisting of a glycolipid, a glycoprotein, proteoglycan and a glycopolymer. In some embodiments, the preparation comprises α-gal epitope mimicking peptides linked to a macromolecule backbone or to another linker and they are capable of binding the anti-Gal antibody. In additional embodiments, said glycolipid comprises α-gal liposomes. In some embodiments, said applying is under conditions such that complement activation within or adjacent to said damaged tissue is enhanced. In further embodiments, said complement activation comprises production of C5a, C4a and C3a. In still further embodiments, said applying is under conditions such that neutrophil recruitment within or adjacent to said injured tissue is enhanced. In additional embodiments, said applying is under conditions such that monocyte and macrophage recruitment within or adjacent to said injured tissue is enhanced. In some embodiments, said applying is under conditions such that repair of said injured tissue is accelerated.

In one embodiment, the present invention contemplates a method, comprising: a) providing: i) a subject having endogenous anti-Gal antibody; ii) damaged pancreatic tissue; and iii) a preparation comprising an α-gal epitope having a terminal galactosyl; b) applying said preparation to said damaged pancreatic tissue to produce treated pancreatic tissue. In further embodiments, said terminal α-galactosyl is selected from the group consisting of Galα1-3Gal and Galα1-6Gal. In still further embodiments, said α-gal epitope is part of a molecule selected from the group consisting of a glycolipid, a glycoprotein, proteoglycan and a glycopolymer. In additional embodiments, said glycolipid comprises α-gal liposomes. In some embodiments, the preparation comprises α-gal epitope mimicking peptides linked to a macromolecule backbone or to another linker and they are capable of binding the anti-Gal antibody. In some embodiments, said applying is under conditions such that complement activation within or adjacent to said damaged tissue is enhanced. In further embodiments, said complement activation comprises production of C5a, C4a and C3a. In still further embodiments, said applying is under conditions such that neutrophil recruitment within or adjacent to said injured tissue is enhanced. In additional embodiments, said applying is under conditions such that monocyte and macrophage recruitment within or adjacent to said injured tissue is enhanced. In some embodiments, said applying is under conditions such that repair of said injured tissue is accelerated.

In some embodiments, the present invention contemplates a method, comprising: a) providing: i) a subject having endogenous anti-Gal antibody; ii) damaged nerve tissue; and iii) a preparation comprising an α-gal epitope having a terminal galactosyl; b) applying said preparation to said damaged nerve tissue to produce treated nerve tissue. In further embodiments, said terminal α-galactosyl is selected from the group consisting of Galα1-3Gal and Galα1-6Gal. In still further embodiments, said α-gal epitope is part of a molecule selected from the group consisting of a glycolipid, a glycoprotein, proteoglycan and a glycopolymer. In additional embodiments, said glycolipid comprises α-gal liposomes. In one embodiment, the preparation comprises α-gal epitope mimicking peptides linked to a macromolecule backbone or to another linker and they are capable of binding the anti-Gal antibody. In some embodiments, said applying is under conditions such that complement activation within or adjacent to said damaged tissue is enhanced. In further embodiments, said complement activation comprises production of C5a, C4a and C3a. In still further embodiments, said applying is under conditions such that neutrophil recruitment within or adjacent to said injured tissue is enhanced. In additional embodiments, said applying is under conditions such that monocyte and macrophage recruitment within or adjacent to said injured tissue is enhanced. In some embodiments, said applying is under conditions such that repair of said injured tissue is accelerated.

In some embodiments, the present invention contemplates a method, comprising: a) providing: i) a subject having endogenous anti-Gal antibody; ii) damaged liver tissue; and iii) a preparation comprising an α-gal epitope having a terminal galactosyl; b) applying said preparation to said damaged liver tissue to produce treated liver tissue. In further embodiments, said terminal α-galactosyl is selected from the group consisting of Galα1-3Gal and Galα1-6Gal. In still further embodiments, said α-gal epitope is part of a molecule selected from the group consisting of a glycolipid, a glycoprotein, a proteoglycan and a glycopolymer. In additional embodiments, said glycolipid comprises α-gal liposomes. In some embodiments, the preparation comprises α-gal epitope mimicking peptides linked to a macromolecule backbone or to another linker and they are capable of binding the anti-Gal antibody. In some embodiments, said applying is under conditions such that complement activation within or adjacent to said damaged tissue is enhanced. In further embodiments, said complement activation comprises production of C5a, C4a and C3a. In still further embodiments, said applying is under conditions such that neutrophil recruitment within or adjacent to said injured tissue is enhanced. In additional embodiments, said applying is under conditions such that monocyte and macrophage recruitment within or adjacent to said injured tissue is enhanced. In some embodiments, said applying is under conditions such that repair of said injured tissue is accelerated.

In some embodiments, the present invention contemplates a method, comprising: a) providing: i) a subject having endogenous anti-Gal antibody; ii) damaged endocrine gland tissue; and iii) a preparation comprising an α-gal epitope having a terminal galactosyl; b) applying said preparation to said damaged endocrine gland tissue to produce treated endocrine gland tissue. In further embodiments, said terminal α-galactosyl is selected from the group consisting of Galα1-3Gal and Galα1-6Gal. In still further embodiments, said α-gal epitope is part of a molecule selected from the group consisting of a glycolipid, a glycoprotein, proteoglycan and a glycopolymer. In additional embodiments, said glycolipid comprises α-gal liposomes. In some embodiments, the preparation comprises α-gal epitope mimicking peptides linked to a macromolecule backbone or to another linker and they are capable of binding the anti-Gal antibody. In some embodiments, said applying is under conditions such that complement activation within or adjacent to said damaged tissue is enhanced. In further embodiments, said complement activation comprises production of C5a, C4a and C3a. In still further embodiments, said applying is under conditions such that neutrophil recruitment within or adjacent to said injured tissue is enhanced. In additional embodiments, said applying is under conditions such that monocyte and macrophage recruitment within or adjacent to said injured tissue is enhanced. In some embodiments, said applying is under conditions such that repair of said injured tissue is accelerated.

In some embodiments, the present invention contemplates a method, comprising: a) providing: i) a subject having endogenous anti-Gal antibody; ii) damaged bone tissue; and iii) a preparation comprising an α-gal epitope having a terminal galactosyl; b) applying said preparation to said damaged bone tissue to produce treated bone tissue. In further embodiments, said terminal α-galactosyl is selected from the group consisting of Galα1-3Gal and Galα1-6Gal. In still further embodiments, said α-gal epitope is part of a molecule selected from the group consisting of a glycolipid, a glycoprotein, proteoglycan and a glycopolymer. In additional embodiments, said glycolipid comprises α-gal liposomes. In some embodiments, the preparation comprises α-gal epitope mimicking peptides linked to a macromolecule backbone or to another linker and they are capable of binding the anti-Gal antibody. In some embodiments, said applying is under conditions such that complement activation within or adjacent to said damaged tissue is enhanced. In further embodiments, said complement activation comprises production of C5a, C4a and C3a. In still further embodiments, said applying is under conditions such that neutrophil recruitment within or adjacent to said injured tissue is enhanced. In additional embodiments, said applying is under conditions such that monocyte and macrophage recruitment within or adjacent to said injured tissue is enhanced. In some embodiments, said applying is under conditions such that repair of said injured tissue is accelerated.

In some embodiments, the present invention contemplates a method, comprising: a) providing: i) a subject having endogenous anti-Gal antibody; ii) damaged cartilage tissue; and iii) a preparation comprising an α-gal epitope having a terminal galactosyl; b) applying said preparation to said damaged cartilage tissue to produce treated cartilage tissue. In further embodiments, said terminal α-galactosyl is selected from the group consisting of Galα1-3Gal and Galα1-6Gal. In still further embodiments, said α-gal epitope is part of a molecule selected from the group consisting of a glycolipid, a glycoprotein, proteoglycan and a glycopolymer. In additional embodiments, said glycolipid comprises α-gal liposomes. In some embodiments, the preparation comprises α-gal epitope mimicking peptides linked to a macromolecule backbone or to another linker and they are capable of binding the anti-Gal antibody. In some embodiments, said applying is under conditions such that complement activation within or adjacent to said damaged tissue is enhanced. In further embodiments, said complement activation comprises production of C5a, C4a and C3a. In still further embodiments, said applying is under conditions such that neutrophil recruitment within or adjacent to said injured tissue is enhanced. In additional embodiments, said applying is under conditions such that monocyte and macrophage recruitment within or adjacent to said injured tissue is enhanced. In some embodiments, said applying is under conditions such that repair of said injured tissue is accelerated.

In one embodiment, the present invention contemplates a method, comprising: a) providing; i) a subject having endogenous anti-Gal antibody and an injured tissue; and ii) a preparation comprising an α-gal epitope having a terminal α-galactosyl as part of a tissue repair and regeneration preparation; and b) applying said preparation to said injury to produce a treated injured tissue. In one embodiment, the tissue is an internal tissue. In one embodiment, the terminal α-galactosyl is selected from the group consisting of Galα1-3Gal, Galα1-2Gal, Galα1-6Gal or any α-galactose sugar units capable of binding anti-Gal antibodies. In one embodiment, the α-gal epitope is free or part of a molecule selected from the group consisting of a natural or synthetic glycolipid, glycoprotein, proteoglycan and a glycopolymer. In additional embodiments, said glycolipid comprises α-gal liposomes. In one embodiment, the preparation comprises α-gal epitope mimicking peptides linked to a macromolecule backbone or to another linker and they are capable of binding the anti-Gal antibody. In one embodiment, the preparation further comprises an injury care device selected from the group consisting of syringes, adhesive bands, compression bandages, sponges, gels, semi-permeable films, plasma clots, fibrin clots. In one embodiment, the device comprises physiological compositions including, but not limited to, solutions, suspensions, emulsions, creams, ointments, aerosol sprays, collagen containing substances, stabilizers, drops, matrix-forming substances, foams and/or dried preparation. In one embodiment, the applying is under conditions such that complement activation within or adjacent to said injured tissue is enhanced. In one embodiment, the complement activation comprises production of complement fragments C5a, C4a and C3a. In one embodiment, the applying is under conditions such that neutrophil recruitment within or adjacent to said injury is enhanced. In one embodiment, the applying is under conditions such that monocyte and macrophage recruitment within or adjacent to said injured tissue is enhanced. In one embodiment, the applying is under conditions such that stem cell recruitment within or adjacent to said injury is enhanced. In one embodiment, the applying is under conditions such that injury healing and tissue repair and regeneration is accelerated.

In one embodiment, the present invention contemplates a method, comprising: a) providing; i) a subject having endogenous anti-Gal antibody and an injured tissue; and ii) a preparation comprising an α-gal liposomes having glycolipids, glycoproteins with a terminal α-galactosyl and comprising α-gal liposomes as part of a tissue repair and regeneration preparation, and/or α-gal epitope mimicking peptides linked to a macromolecule backbone or to another linker and they are capable of binding the anti-Gal antibody and comprising α-gal liposomes; and b) applying said preparation to said injury to produce a treated injured tissue. In one embodiment, the preparation further comprises an injury care device selected from the group consisting of syringes, adhesive bands, compression bandages, sponges, gels, semi-permeable films, plasma clots, fibrin clots. In one embodiment, the device comprises physiological compositions including, but not limited to, solutions, suspensions, emulsions, creams, ointments, aerosol sprays, collagen containing substances, stabilizers, drops, matrix-forming substances, foams and/or dried preparation. In one embodiment, the preparation further comprises anti-Gal antibodies bound to said α-gal liposomes. In one embodiment, the applying is under conditions such that complement activation within or adjacent to said injured tissue is enhanced. In one embodiment, the complement activation comprises production of complement fragments C5a, C4a and C3a. In one embodiment, the applying is under conditions such that neutrophil recruitment within or adjacent to said injured tissue is enhanced. In one embodiment, the applying is under conditions such that monocyte and macrophage recruitment within or adjacent to said injured tissue is enhanced. In one embodiment, the applying is under conditions such that stem cell recruitment within or adjacent to said injury is enhanced. In one embodiment, the applying is under conditions such that injury healing and tissue repair and regeneration is accelerated.

In one embodiment, the present invention contemplates a method, comprising: a) providing; i) a subject having endogenous anti-Gal antibody and one or more of an injured tissue including, but not limited to, brain tissue, nerve tissue, eye tissue, gastrointestinal tissue, muscle tissue, cartilage tissue, bone tissue, endocrine glands and vascular tissue; ii) a preparation comprising an α-gal epitope having a terminal α-galactosyl as part of a tissue repair and regeneration preparation; and b) applying said preparation to said injured tissue to produce a treated injured tissue. In one embodiment, the terminal α-galactosyl is selected from the group consisting of Galα1-3Gal, Galα1-2Gal, Galα1-6Gal and any α-galactose sugar units capable of binding anti-Gal antibodies. In one embodiment, the α-gal epitope is free or part of a molecule selected from the group consisting of a natural or synthetic glycolipid, glycoprotein, and a glycopolymer. In one embodiment, the preparation comprises α-gal liposomes. In one embodiment, the preparation comprises α-gal epitope mimicking peptides linked to a macromolecule backbone or to another linker and they are capable of binding the anti-Gal antibody. In one embodiment, the preparation further comprises an injury care device selected from the group consisting of syringes, adhesive bands, compression bandages, sponges, gels, semi-permeable films, plasma clots, fibrin clots. In one embodiment, the device comprises physiological compositions including, but not limited to, solutions, suspensions, emulsions, creams, ointments, aerosol sprays, collagen containing substances, stabilizers, drops, matrix-forming substances, foams and/or dried preparation. In one embodiment, the preparation further comprises anti-Gal antibodies bound to said α-gal liposomes. In one embodiment, the applying is under conditions such that complement activation within or adjacent to said injured tissue is enhanced. In one embodiment, the complement activation comprises production of complement fragments C5a, C4a and C3a. In one embodiment, the applying is under conditions such that neutrophil recruitment within or adjacent to said injured tissue is enhanced. In one embodiment, the applying is under conditions such that monocyte and macrophage recruitment within or adjacent to said injured tissue is enhanced. In one embodiment, the applying is under conditions such that stem cell recruitment within or adjacent to said injury is enhanced. In one embodiment, the applying is under conditions such that injury healing and tissue repair and regeneration is accelerated.

In one embodiment, the present invention contemplates a method, comprising: a) providing; i) a subject having endogenous anti-Gal antibody and having diabetes in which insulin production is impaired; and ii) a preparation comprising an α-gal epitope having a terminal α-galactosyl as part of a tissue repair and regeneration preparation; and b) applying said preparation into the pancreas of said subject to induce regeneration of Langerhans Islets and production of endogenous insulin. In one embodiment, the terminal α-galactosyl is selected from the group consisting of Galα1-3Gal, Galα1-2Gal, Galα1-6Gal and any α-galactose sugar units capable of binding anti-Gal antibodies. In one embodiment, the α-gal epitope is free or part of a molecule selected from the group consisting of a natural or synthetic glycolipid, glycoprotein, and a glycopolymer. In one embodiment, the preparation comprises α-gal liposomes. In one embodiment, the preparation comprises α-gal epitope mimicking peptides linked to a macromolecule backbone or to another linker and they are capable of binding the anti-Gal antibody. In one embodiment, the preparation further comprises an injury care device selected from the group consisting of syringes, adhesive bands, compression bandages, sponges, gels, semi-permeable films, plasma clots, fibrin clots. In one embodiment, the device comprises physiological compositions including, but not limited to, solutions, suspensions, emulsions, creams, ointments, aerosol sprays, collagen containing substances, stabilizers, drops, matrix-forming substances, foams and/or dried preparation. In one embodiment, the preparation further comprises anti-Gal antibodies bound to said α-gal liposomes. In one embodiment, the applying is under conditions such that complement activation within or adjacent to said injured tissue is enhanced. In one embodiment, the complement activation comprises production of complement fragments C5a, C4a and C3a. In one embodiment, the applying is under conditions such that neutrophil recruitment within pancreas is enhanced. In one embodiment, the applying is under conditions such that monocyte and macrophage recruitment pancreas is enhanced. In one embodiment, the applying is under conditions such that stem cell recruitment within pancreas is enhanced. In one embodiment, the recruited stem cells differentiate into Langerhans Islet cells. In one embodiment, the Langerhans Islet cells produce insulin.

In one embodiment, the present invention contemplates a method, comprising: a) providing; i) a subject having endogenous anti-Gal antibody and having injury in a peripheral nerve, spinal cord, blood vessel or any other tissue: ii) a device comprising a biodegradable or non-biodegradable sheet coated with or containing a preparation comprising an α-gal epitope having a terminal α-galactosyl as part of a tissue repair and regeneration preparation; and b) applying said sheet around said injured nerve, spinal cord, blood vessel, or other tissue to produce a treated injured tissue. In one embodiment, the terminal α-galactosyl is selected from the group consisting of Galα1-3Gal, Galα1-2Gal, Galα1-6Gal and any α-galactose sugar units capable of binding anti-Gal antibodies. In one embodiment, the α-gal epitope is free or part of a molecule selected from the group consisting of a natural or synthetic glycolipid, glycoprotein, and a glycopolymer. In one embodiment, the preparation comprises α-gal liposomes. In one embodiment, the preparation comprises α-gal epitope mimicking peptides linked to a macromolecule backbone or to another linker and they are capable of binding the anti-Gal antibody. In one embodiment, the preparation is part of a injury care device selected from the group consisting of collagen containing sheet, synthetic sheet, or any other sheet that can be wrapped around the injured nerve, spinal cord, blood vessel, or other injured tissue. In one embodiment, the preparation further comprises anti-Gal antibodies bound to said α-gal liposomes. In one embodiment, the applying is under conditions such that complement activation within or adjacent to said injured tissue is enhanced. In one embodiment, the complement activation comprises production of complement fragments C5a, C4a and C3a. In one embodiment, the applying is under conditions such that neutrophil recruitment to the injured tissue is enhanced. In one embodiment, the applying is under conditions such that monocyte and macrophage recruitment to the injured tissue is enhanced. In one embodiment, the applying is under conditions such that stem cell recruitment to the injured tissue is enhanced. In one embodiment, the recruited stem cells differentiate into cells that repair the injured tissue.

In some embodiments, the invention relates to a method, comprising: a) providing: i) a subject having endogenous anti-Gal antibody; ii) a wound; and iii) a preparation comprising an α-gal epitope having a terminal galactosyl; and b) applying said preparation to said wound to produce a treated wound. In further embodiments, said terminal α-galactosyl is selected from the group consisting of Galα1-3Gal, and Galα1-6Gal. In still further embodiments, said α-gal epitope is part of a molecule selected from the group consisting of a glycolipid, a glycoprotein, and a glycopolymer. In additional embodiments, said glycolipid comprises α-gal liposomes. In one embodiment, the preparation comprises α-gal epitope mimicking peptides linked to a macromolecule backbone or to another linker and they are capable of binding the anti-Gal antibody. In some embodiments, said applying is under conditions such that complement activation within or adjacent to said wound is enhanced. In further embodiments, said complement activation comprises production of C5a, C4a and C3a. In still further embodiments, said applying is under conditions such that neutrophil recruitment within or adjacent to said wound is enhanced. In additional embodiments, said applying is under conditions such that monocyte and macrophage recruitment within or adjacent to said wound is enhanced. In some embodiments, said applying is under conditions such that wound closure is accelerated. In further embodiments, the method is used to treat subjects diagnosed with or exhibiting symptoms associated with heart disease and damage, arthritis, osteoarthritis, cartilage repair and diabetes mellitus. In still further embodiments, the disclosed method is used to treat tissue or organ damage in combination with the application of stem cells.

In some embodiments the invention relates to a method, comprising: a) providing; i) a subject having a wound; ii) a wound care device comprising a preparation comprising an α-gal epitope having a terminal α-galactosyl, and iii) an anti-Gal antibody; and b) applying said wound care device to said wound to produce a treated wound. In further embodiments, said terminal α-galactosyl is selected from the group consisting of Galα1-3Gal, Galα1-2Gal and Galα1-6Gal. In still further embodiments, said α-gal epitope is part of a molecule selected from the group consisting of a glycolipid, a glycoprotein, and a glycopolymer. In additional embodiments, said glycolipid comprises α-gal liposomes. In one embodiment, the preparation comprises α-gal epitope mimicking peptides linked to a macromolecule backbone or to another linker and they are capable of binding the anti-Gal antibody. In some embodiments, said preparation is part of a wound care device selected from the group consisting of adhesive bands, compression bandages, gels, semi-permeable films, and foams. In further embodiments, the disclosed method and preparation is used to treat subjects diagnosed with or exhibiting symptoms associated with heart disease and damage, arthritis, osteoarthritis, cartilage repair and diabetes mellitus. In still further embodiments, the disclosed method and preparation is used to treat tissue or organ damage in combination with the application of stem cells.

In some embodiments, the invention relates to a burn care device comprising a preparation comprising an α-gal epitope having a terminal α-galactosyl. In further embodiments, said terminal α-galactosyl is selected from the group consisting of Galα1-3Gal, and Galα1-6Gal. In still further embodiments, said α-gal epitope is part of a molecule selected from the group consisting of a glycolipid, a glycoprotein, and a glycopolymer. In additional embodiments, said glycolipid comprises α-gal liposomes. In one embodiment, the preparation comprises α-gal epitope mimicking peptides linked to a macromolecule backbone or to another linker and they are capable of binding the anti-Gal antibody. In some embodiments, said preparation further comprises anti-Gal antibodies bound to said α-gal liposomes. In further embodiments, said device is in the form of one of the group consisting of adhesive bands, compression bandages, gels, semipermeable films, and foams. In further embodiments, the disclosed device and preparation is used to treat subjects diagnosed with or exhibiting symptoms associated with heart disease and damage, arthritis, osteoarthritis, cartilage repair and diabetes mellitus. In still further embodiments, the disclosed device and preparation is used to treat tissue or organ damage in combination with the application of stem cells.

In some embodiments, the invention relates to a method, comprising: a) providing: i) a subject having endogenous anti-Gal antibody; and ii) damaged cardiac tissue; and iii) a preparation comprising an α-gal epitope having a terminal galactosyl; b) applying said preparation to said damaged cardiac tissue to produce treated cardiac tissue. In further embodiments, said terminal α-galactosyl is selected from the group consisting of Galα1-3Gal, Galα1-2Gal and Galα1-6Gal. In still further embodiments, said α-gal epitope is part of a molecule selected from the group consisting of a glycolipid, a glycoprotein, and a glycopolymer. In additional embodiments, said glycolipid comprises α-gal liposomes. In some embodiments, the preparation comprises α-gal epitope mimicking peptides linked to a macromolecule backbone or to another linker and they are capable of binding the anti-Gal antibody. In some embodiments, said applying is under conditions such that complement activation within or adjacent to said damaged cardiac tissue is enhanced. In further embodiments, said complement activation comprises production of C5a, C4a and C3a. In still further embodiments, said applying is under conditions such that neutrophil recruitment within or adjacent to said damaged cardiac tissue is enhanced. In additional embodiments, said applying is under conditions such that monocyte and macrophage recruitment within or adjacent to said damaged cardiac tissue is enhanced. In some embodiments, said applying is under conditions such that repair of said damaged cardiac tissue is accelerated.

In some embodiments, the invention relates to a method, comprising: providing a subject having endogenous anti-Gal antibody and tissue damaged by diabetes; and a preparation comprising an α-gal epitope having a terminal galactosyl; and applying said preparation to said tissue damaged by diabetes to produce treated tissue. In further embodiments, said terminal α-galactosyl is selected from the group consisting of Galα1-3Gal, Galα1-2Gal, and Galα1-6Gal. In still further embodiments, said α-gal epitope is part of a molecule selected from the group consisting of a glycolipid, a glycoprotein, and a glycopolymer. In additional embodiments, said glycolipid comprises α-gal liposomes. In some embodiments, the preparation comprises α-gal epitope mimicking peptides linked to a macromolecule backbone or to another linker and they are capable of binding the anti-Gal antibody. In some embodiments, said applying is under conditions such that complement activation within or adjacent to said tissue damaged by diabetes is enhanced. In further embodiments, said complement activation comprises production of C5a and C3a. In still further embodiments, said applying is under conditions such that neutrophil recruitment within or adjacent to said tissue damaged by diabetes is enhanced. In additional embodiments, said applying is under conditions such that monocyte and macrophage recruitment within or adjacent to said tissue damaged by diabetes is enhanced. In some embodiments, said applying is under conditions such that repair of said tissue damaged by diabetes is accelerated.

In some embodiments, the invention relates to a method, comprising: providing a subject having endogenous anti-Gal antibody and tissue damaged by osteoarthritis; and a preparation comprising an α-gal epitope having a terminal galactosyl; and applying said preparation to said tissue damaged by osteoarthritis to produce treated tissue. In further embodiments, said terminal α-galactosyl is selected from the group consisting of Galα1-3Gal, Galα1-2Gal and Galα1-6Gal. In still further embodiments, said α-gal epitope is part of a molecule selected from the group consisting of a glycolipid, a glycoprotein, and a glycopolymer. In additional embodiments, said glycolipid comprises α-gal liposomes. In some embodiments, the preparation comprises α-gal epitope mimicking peptides linked to a macromolecule backbone or to another linker and they are capable of binding the anti-Gal antibody. In some embodiments, said applying is under conditions such that complement activation within or adjacent to said tissue damaged by osteoarthritis is enhanced. In further embodiments, said complement activation comprises production of C5a, C4a and C3a. In still further embodiments, said applying is under conditions such that neutrophil recruitment within or adjacent to said tissue damaged by osteoarthritis is enhanced. In additional embodiments, said applying is under conditions such that monocyte and macrophage recruitment within or adjacent to said tissue damaged by osteoarthritis is enhanced. In some embodiments, said applying is under conditions such that repair of said tissue damaged by osteoarthritis is accelerated. In further embodiments, said tissue damaged by osteoarthritis is selected from the group consisting of bone and cartilage.

BRIEF DESCRIPTION OF THE DRAWINGS

The following are illustrations of the present invention and are not intended to limit the scope of the invention in any manner.

FIG. 2 shows the components of α-gal liposomes prepared from rabbit red blood cell (RBC) membranes.

FIG. 3 shows the binding of anti-Gal to α-gal liposomes either in an in vitro suspension or in a solid-phase antigen in an enzyme-linked immunosorbent assay (ELISA).

FIG. 4 shows the activation of human complement or rabbit complement by human anti-Gal binding to α-gal epitopes on α-gal liposomes.

FIG. 6A shows untreated skin with the epidermis containing one or two layers of epithelial cells, and the dermis containing fibroblasts and fat cells (×100). FIG. 6B shows skin 12 hours post-injection (×100). FIG. 6C shows skin 12 h post-injection with the injection site at the center of the figure (×100). FIG. 6D shows skin 12 h post-injection (×400). Higher magnification of the infiltrating inflammatory cells indicates that the cells are neutrophils, based on the morphological characteristics of their nuclei. FIG. 6E shows skin 48 h post-injection (×400). The infiltrating inflammatory cells at this time point are mononuclear cells with characteristics of macrophages, as indicated by the kidney shape of many of these cells. FIG. 6F shows skin five days post-injection (×100). Most macrophages assume a round morphology because of internalization of numerous α-gal liposomes. The area in the center of the injection site is devoid of cells and is functioning as an α-gal liposome depot. FIG. 6G shows skin 14 days post-injection (×100) with macrophages still visible in area of the injection site. FIG. 6H shows skin 20 days post-injection (×100). The injection area contains many myofibroblasts differentiating into fibroblasts or muscle cells, and almost no macrophages are observed within the injected area.

FIG. 12A. Heart injected with saline obtained 2 week post implantation. Note the necrotic cardiomyocytes and the infiltrating neutrophils (×100).

FIG. 12B. Heart injected with α-gal liposomes obtained 2 week post implantation. Note the large number of infiltrating macrophages (×100).

FIG. 12C. As FIG. 12B, however the implanted heart was removed after 4 weeks. Note the border between the site of the α-gal liposomes injection (lower half) and the non-injected area which contains migrating macrophages (×200).

FIG. 12D. An area of the myocardium in α-gal liposomes injected hearts which lacks infiltrating cells, 2 weeks post implantation. Note that no nuclei are detected in the dead cardiomyocytes (×100).

FIG. 13A: Muscle fibers in an uninjured skeletal muscle comprising muscle cell syncitia (myotubes), formed by fusion of myoblasts, with nuclei in the periphery of the tubes.

FIG. 13B: Ischemia-induced myotube death after 96 hours, showing the resulting necrosis after sham injection with saline to serve as control to α-gal liposomes injection. Neutrophil infiltration of the necrotic tissue may be observed. Decreased myotube syncitia size is also observed wherein the nuclei of each myotube accumulate in a row. Subsequently, the dead myotubes are phagocytosed by debriding macrophages.

FIG. 13C: Ischemia-induced myotube death after 96 hours, showing improved structure after injection with 10 mg α-gal liposomes (H&E ×200).

FIG. 14A. Cells obtained from the subcutaneously implanted PVA sponge, 6 days post implantation. Most cells have the morphology of activated macrophages. The multiple vacuoles represent α-gal liposomes internalized by the macrophages. The bar represents 10 μm (×500).

FIGS. 14B and 14C: Infiltrating macrophage populations also include cells that display an extensive ability to proliferate, i.e., to self renew, resulting in 200-500 cells per colony formed from one cell within a period of 5 days. Note the multiple mitotic cells in FIG. 14B. The frequency of these colony forming cells among cultured macrophages from PVA sponges is 3-5 cells/$10^5$ macrophages. The colonies are representative of similar colonies from infiltrating macrophages in 5 mice.

DEFINITIONS

Figure 1A:
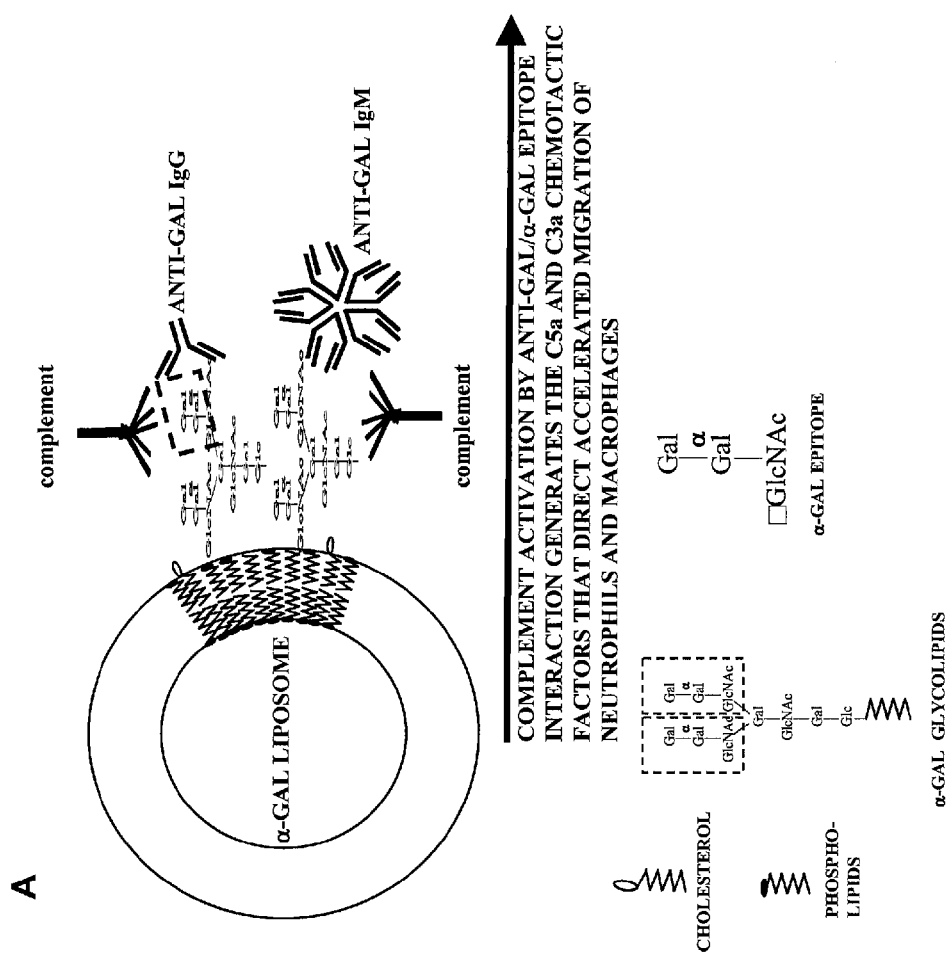
FIG. 1A shows an interaction of an α-gal liposome with anti-Gal IgG and IgM antibodies.

To facilitate an understanding of the present invention, a number of terms and phrases are defined below:

The term "α-gal epitope" as used herein, refers to any molecule, or part of a molecule, with a terminal structure comprising Galα1-3Galβ1-4GlcNAc-R, Galα1-3Galβ1-3 GlcNAc-R, or any carbohydrate chain with terminal Galα1-3Gal at the non-reducing end, or any molecule with terminal α-galactosyl unit capable of binding the anti-Gal antibody.

The term "glycolipid" as used herein, refers to any molecule with at least one carbohydrate chain linked to a ceramide, or a fatty acid chain, or any other lipid. Alternatively, a glycolipid maybe referred to as a glycosphingolipid.

The term "α-gal glycolipid" as used herein, refers to any glycolipid that has at least one α-gal epitope on its nonreducing end of the carbohydrate chain.

The term "α-gal epitope mimicking peptides" as used herein, refers to any peptide that is capable of binding the anti-Gal antibody.

The term "α-gal liposomes" as used herein, refers to any liposomes that have α-gal epitopes and are capable of binding the anti-Gal antibody.

The term "α-gal ointment" as used herein, refers to any ointment of hydrocarbon base or any other base that contains α-gal epitopes in a free form or α-gal epitopes in α-gal glycolipids, α-gal proteins, or α-gal polymers.

As used herein, the term "purified" refers to molecules (polynucleotides, or polypeptides, or glycolipids) that are removed from their natural environment, isolated or separated. "Substantially purified" molecules are at least 50% free, preferably at least 75% free, more preferably at least 90% and most preferably at least 95% free from other components with which they are naturally associated.

The terms "α1,3-galactosyltransferase," "α-1,3-galactosyltransferase," "α1,3GT," "glycoprotein α-galactosyltransferase 1" and "GGTA1," as used herein refer to any enzyme capable of synthesizing α-gal epitopes. The enzyme is expressed in most mammals with the exception of humans, apes and Old World monkeys. The carbohydrate structure produced by the enzyme is immunogenic in man and most healthy people have high titer natural anti α-gal antibodies, also referred to as "anti-Gal" antibodies. In some embodiments, the term "α1,3GT" refers to a common marmoset gene (e.g., *Callithrix jacchus*—GENBANK Accession No. S71333) and its gene product, as well as its functional mammalian counterparts (e.g., other New World monkeys, prosimians and non-primate mammals, but not Old World monkeys, apes and humans). The term "α1,3GT" is in no way limited to a particular mammal, for example, the term may include mouse α1,3GT (e.g., *Mus musculus*—nucleotides 445 to 1560 of GENBANK Accession No. NM_010283), bovine α1,3GT (e.g., *Bos taurus*—GENBANK Accession No. NM_177511), feline α1,3GT (e.g., *Felis catus*—GENBANK Accession No. NM_001009308), ovine α1,3GT (e.g., *Ovis aries*—GENBANK Accession No. NM_001009764), rat α1,3GT (e.g., *Rattus norvegicus*—GENBANK Accession No. NM_145674) and porcine α1,3GT (e.g., *Sus scrofa*—GENBANK Accession No. NM_213810). Some embodiments of the present invention comprise a functional variant of a mammalian α1,3GT, which differs from the wild type mammalian α1,3GT sequences in, for example, fewer than 1-5% of the residues. α1,3GT variants include but are in no way limited to naturally occurring, functional mammalian α1,3GT variants, as well as non-naturally occurring variants generated by recombinant or other means (e.g., 1, 2, 3, 4 or 5 amino acid substitutions, deletions, or additions, preferably corresponding to a residue from a functional mammalian α1,3GT homolog) are contemplated to find use in the compositions and methods of the present invention. In other embodiments, truncated forms of a mammalian α1,3GT, which retain catalytic activity, are employed (e.g., GGTA1 lacking 90 amino acid N-terminal stem region).

The term "anti-Gal binding epitope", as used herein, refers to any molecule or part of molecule that is capable of binding in vivo the natural anti-Gal antibody.

The term "isolated" as used herein, refers to any composition or mixture that has undergone a laboratory purification procedure including, but not limited to, extraction, centrifugation and chromatographic separation (e.g., thin layer chromatography or high performance liquid chromatography). Usually such a purification procedures provides an isolated composition or mixture based upon physical, chemical, or electrical potential properties. Depending upon the choice of procedure an isolated composition or mixture may contain other compositions, compounds or mixtures having similar chemical properties.

The term "control" refers to subjects or samples which provide a basis for comparison for experimental subjects or samples. For instance, the use of control subjects or samples permits determinations to be made regarding the efficacy of experimental procedures. In some embodiments, the term "control subject" refers to animals, which receive a mock treatment (e.g., saline).

The term "diabetic" as used here refers to organisms which have a disorder characterized by the insufficient production or utilization of insulin. Insulin is a pancreatic hormone that is needed to convert glucose for cellular metabolism and energy production. In preferred embodiments of the present invention, the term "diabetic patient" refers to patients suffering from diabetes mellitus. The term "diabetic" encompasses both patients with type I diabetes (juvenile onset) and patients with type II diabetes (adult onset). "Type I diabetes" also referred to as "insulin-dependent diabetes" is a form of diabetes mellitus that usually develops during childhood or adolescence and is characterized by a severe deficiency in insulin secretion resulting from atrophy of the islets of Langerhans and causing hyperglycemia and a marked tendency towards ketoacidosis. "Type II diabetes" also referred to as "non-insulin-dependent diabetes" is a form of diabetes mellitus that develops especially in adults (most often in obese individuals) and that is characterized by hyperglycemia resulting from both insulin-resistance and an inability to produce more insulin.

The term "aged" as used herein refer to older human subjects (e.g., middle age and above of 50 years and older, senior citizen and above of 65 years and older, or elderly and above of 80 years and older, etc.). The term "aged" also encompass older nonhuman mammalian subjects at similar stages in their life cycles (e.g., 8-12 years and older for cats and large dogs, 10-15 years and older for small and medium sized dogs, 15-18 months and older for mice, etc.)

The terms "patient" and "subject" refer to a mammal or an animal that is a candidate for receiving medical treatment.

As used herein, the term "wound" refers to a disruption of the normal continuity of structures caused by a physical (e.g., mechanical) force, a biological (e.g., thermic or actinic force, or a chemical means. In particular, the term "wound" encompasses wounds of the skin. The term "wound" also encompasses contused wounds, as well as incised, stab, lacerated, open, penetrating, puncture, abrasions, grazes, burns, frostbites, corrosions, wounds caused by ripping, scratching, pressure, and biting, and other types of wounds. In particular, the term encompasses ulcerations (i.e., ulcers), preferably ulcers of the skin.

As used herein, the term "wound healing" refers to a regenerative process with the induction of an exact temporal and spatial healing program comprising wound closure and the processes involved in wound closure. The term "wound healing" encompasses but is not limited to the processes of granulation, neovascularization, fibroblast, endothelial and epithelial cell migration, extracellular matrix deposition, re-epithelialization, and remodeling.

The term "wound closure" refers to the healing of a wound wherein sides of the wound are rejoined to form a continuous barrier (e.g., intact skin).

The term "granulation" refers to the process whereby small, red, grain-like prominences form on a raw surface (that of wounds or ulcers) as healing agents.

The term "neovascularization" refers to the new growth of blood vessels with the result that the oxygen and nutrient supply is improved. Similarly, the term "angiogenesis" refers to the vascularization process involving the development of new capillary blood vessels.

The term "cell migration" refers to the movement of cells (e.g., fibroblast, endothelial, epithelial, etc.) to the wound site.

The term "extracellular matrix deposition" refers to the secretion by cells of fibrous elements (e.g., collagen, elastin, reticulin), link proteins (e.g., fibronectin, laminin), and space filling molecules (e.g., glycosaminoglycans). As used herein, the term "type I collagen" refers to the most abundant collagen, which forms large well-organized fibrils having high tensile strength.

The term "re-epithelialization" refers to the reformation of epithelium over a denuded surface (e.g., wound).

The term "remodeling" refers to the replacement of and/or devascularization of granulation tissue.

The term "impaired healing capabilities" comprises wounds, which are characterized by a disturbed wound healing process. Examples of wounds with impaired healing capabilities are wounds of diabetic patients and alcoholics, wounds which are infected by microorganisms, ischemic wounds, wounds of patients suffering from deficient blood supply or venous stasis, and ulcers. Particularly preferred wounds are diabetic wounds. Other preferred wounds include wounds of elderly subjects and chronic wounds of subjects of any age.

As used herein, the term "chronic wound" refers to a wound that does not fully heal even after a prolonged period of time (e.g., 2 to 3 months or longer).

The term "diabetic wounds" refers to wounds of mammals and humans suffering from diabetes. An example of a diabetic wound is an ulcer (e.g., *Ulcus cruris arteriosum* or *Necrobiosis lipoidica*).

As used herein, the term "ulcer" (i.e., "ulceration") refers to a local defect or excavation of the surface of an organ or tissue, produced by sloughing of necrotic tissue. The term encompasses various forms of ulcers (e.g., diabetic, neuropathic, arterial, decubitus, dental, perforating, phagedenic, rodent, trophic, tropical, varicose, venereal, etc.), although in preferred embodiments, surface (i.e., skin) ulcers are involved in the present invention. Especially preferred ulcers are diabetic ulcers.

In some embodiments, the present invention provides methods and compositions for "accelerating wound healing," whereby different aspects of the wound healing process are "enhanced." As used herein, the term "enhanced" indicates that the methods and compositions provide an increased rate of wound healing. In preferred embodiments, the term "enhanced" indicates that the wound healing rate and/or a wound healing process occurs at least 10% faster than is observed in untreated or control-treated wounds. In particularly preferred embodiments, the term "enhanced" indicates that the wound healing rate and/or a wound healing process occurs at least 15% faster than is observed in untreated or control-treated wounds. In still further preferred embodiments, the term "enhanced" indicates that the wound healing rate and/or a wound healing process occurs at least 20% (e.g., 50%, 100%, . . . ) faster than wounds untreated or control-treated wounds.

As used herein, the terms "localized" and "local" refer to the involvement of a limited area. Thus, in contrast to "systemic" treatment, in which the entire body is involved, usually through the vascular and/or lymph systems, localized treatment involves the treatment of a specific, limited area. Thus, in some embodiments, discrete wounds are treated locally using the methods and compositions of the present invention.

As used herein, the term "topically" means application to the surface of the skin, mucosa, viscera, etc. Similarly, the terms "topically active drug" and "topically active agent" refer to a substance or composition, which elicits a pharmacologic response at the site of application (e.g., skin), but is not necessarily an antimicrobial agent.

As used herein, the term "medical devices" includes any material or device that is used on, in, or through a patient's body in the course of medical treatment for a disease or injury. Medical devices include, but are not limited to, such items as medical implants, wound care devices, drug delivery devices, and body cavity and personal protection devices. The medical implants include, but are not limited to, urinary catheters, intravascular catheters, dialysis shunts, wound drain tubes, skin sutures, vascular grafts, implantable meshes, intraocular devices, heart valves, and the like.

As used herein, "wound care devices" and "burn care devices" include, but are not limited to conventional materials such as dressings, plasters, compresses, ointments containing the pharmaceuticals, or gels containing the pharmaceuticals that can be used in accordance with the present invention. Thus, it is possible to administer the wound care devices comprising α-gal epitopes or α-gal epitopes and anti-Gal antibodies topically and locally in order to exert an immediate and direct effect on wound healing. The topical administration of wound care devices can be effected, for example, in the form of a solution, an emulsion, a cream, an ointment, a foam, an aerosol spray, a gel matrix, a sponge, drops or washings. Suitable additives or auxiliary substances are isotonic solutions, such as physiological sodium chloride solutions or sodium alginate, demineralized water, stabilizers, collagen containing substances such as Zyderm II or matrix-forming substances such as povidone. To generate a gel basis, formulations, such as aluminum hydroxide, polyacrylacid derivatives, and cellulose derivatives (e.g., carboxymethyl cellulose), fibrin clot, and plasma clots are suitable. These gels can be prepared as hydrogels on a water basis or as oleogels with low and high molecular weight paraffines or Vaseline and/or yellow or white wax. As emulsifier alkali soaps, metal soaps, amine soaps or partial fatty acid esters of sorbitants can be used, whereas lipids can be added as Vaseline, natural and synthetic waxes, fatty acids, mono-, di-, triglycerides, paraffin, natural oils or synthetic fats. The wound care devices comprising α-gal epitopes and anti-Gal antibodies according to the invention can also, where appropriate, be administered topically and locally, in the region of the wound, in the form of liposome/antibody complexes, or complexes between any antigen and its corresponding antibody, or complement activating substances.

Furthermore, the treatment can be effected using a transdermal therapeutic system (TTS), which enables the pharmaceuticals of the present invention to be released in a temporally controlled manner. To improve the penetration of the administered drug through the membrane, additives such as ethanol, urea or propylene glycol can be added in addition to polymeric auxiliaries.

The term "fibrin clot" refers to any mass, mesh, plug comprising isolated fibrinogen mixed with thrombin and thus induced to convert into fibrin that is non globular and forms a clot.

The term "plasma clot" refers to plasma mixed with an agent inducing conversion of fibrinogen within the plasma into non globular fibrin, thereby forming a clot.

The term "soluble" refers to any ability of a compound to completely dissolve within a solution. Usually, but not exclusively, the compound may be a salt that dissociates into a cationic and anionic species. Nonetheless, it would be expected that a fully soluble compound comprises a monomeric species.

The term "physiological composition" or "pharmaceutical composition" as used herein, are clinically acceptable (i.e., for example, antiseptic, sterile, non-inflammatory, non-allergenic) such they can be administered internally and/or externally and may comprise any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such compositions.

DETAILED DESCRIPTION OF THE INVENTION

The present invention is related to the field of wound healing. In particular, the present invention provides compositions and methods comprising molecules with linked α-gal epitopes for induction of an inflammatory response localized within or surrounding damaged tissue. In some embodiments, the present invention provides treatments for tissue repair in normal subjects and in subjects having impaired healing capabilities, such as diabetic and aged subjects.

In some embodiments, the invention relates to methods and compositions for the promotion of wound healing. Macrophages play a major role in the success of wound healing in part by generation of reactive radicals such as nitric oxide and oxygen peroxide, and through the secretion of collagenase and elastase as provided for in Bryant et al., *Prog. Clin. Biol. Res.* 266, 273 (1988) and Knighton et al., *Prog. Clin. Biol. Res.* 299, 217 (1989), both of which are hereby incorporated by reference. Macrophages secrete cytokines and growth factors that are essential in recruitment of macrophages, lymphocytes, mesenchimal stem cells and fibroblasts into the wound site. Cytokines and growth factors also regulate fibroblast and epithelial cell proliferation, as well as proliferation of endothelial cells for revascularization as disclosed in Rappolee et al., *Curr. Top. Microbiol. Immunol.* 181, 87 (1992) and Nathan, *J. Clin. Invest.* 79, 319 (1987), both of which are hereby incorporated by reference. Accordingly, experiments in macrophage-depleted animals have been associated with defects in wound healing as provided for in Leibovich and Ross, *Am. J. Pathol.* 78, 71 (1975), incorporated in its entirety by reference.

Accelerated wound healing and improved repair and remodeling of damaged tissues is contemplated to be achievable by effectively controlling recruitment of monocytes and differentiation of these cells into activated macrophages. Activated macrophages in turn secrete fibrogenic and angiogenic growth factors inducing formation of granulation tissue containing myofibroblasts as described in Frangogiannis, *Curr. Med. Chem.* 13, 1877 (2006), incorporated herein by reference, and angiogenesis associated with local collagen synthesis and re-epithelization as provided for in Stein et al., *Clin. Exp. Allergy* 22, 19 (1992); DiPietro, *Shock* 4, 233 (1995); Clark, *J. Dermatol. Surg. Oncol.* 19, 693 (1993) and Rappolee et al., *Curr. Topics Microbial Immunol.* 181, 87 (1992), all of which are hereby incorporated by reference. Macrophages have key functions in almost every stage of the wound healing, tissue repair and remodeling processes. Upon initiation of the inflammatory stage, macrophages secrete interleukin-1 (IL-1), which induces the rapid recruitment of inflammatory cells from the circulation into the wound as provided for in Dinarello, *FASEB J.* 2, 108 (1988), incorporated in its entirety by reference. As phagocytes, the macrophages aid in the digestion of bacteria and cell debris as described in Aderem et al., *Ann. Rev. Immunol.* 17, 593 (1999), incorporated herein by reference. In later stages, macrophages secrete interleukin-6 (IL-6), which influences endothelial cell proliferation and initiation of angiogenesis as discussed in Mateo et al., *Am. J. Physiol.* 266, R1840 (1994), hereby incorporated by reference. Macrophages further coordinate cellular proliferation by production of growth factors such as α and β vascular endothelial cell growth factors (VGEF), epidermal growth factor (EGF), fibroblast growth factor (FGF) and insulin-like growth factor (IGF) as provided for in Singer et al., *New England Journal of Medicine* 341, 738 (1999), incorporated herein by reference. Moreover, local administration of in vitro activated macrophages into ulcerated wounds, or into wounds resulting from infections following open heart surgery, was found to accelerate the wound healing process as described in Danon et al., *Exp. Gerontol.* 32, 633 (1997) and Orensterin et al., *Wound Repair Regen.* 13, 237 (2005), both of which are incorporated in their entirety by reference.

An additional characteristic attributed to recruited macrophage is the ability of a small proportion of them to function as stem cells. It has been reported that monocytes/macrophages include a small population of multipotential stem cells that can proliferate and undergo trans-differentiation into various types of cells, based on microenvironment and on the adjacent cells. Seta et al., *Keio J Med.* 56:41 (2007). For example, incubation of human macrophages in presence of chicken cardiomyocytes results in differentiation of a small proportion of cells into human cardiomyocytes. Similarly, incubation of human macrophages with rat fetal neurons results in induction of human stem cells among macrophages to differentiate into neurons. Macrophages are capable of recruiting stem cells from the adjacent uninjured tissue or from other sites in the body, and/or macrophages trans-differentiate into stem cells. The recruitment and activation by the treatment of injection of α-gal liposomes into injured tissues results in rapid migration of stem cells into treated injured tissue and in accelerated repair and regeneration of the injured tissue for the restoration of its pre-injury biological activity. As illustrated in FIG. 1, this recruitment and activation is the result of the interaction between the natural anti-Gal antibody and α-gal epitopes on the injected α-gal liposomes and the subsequent Fc/FcγR interaction between macrophages and the anti-Gal bound to α-gal liposomes.

In some embodiments, the present invention provides for compositions and methods for using the anti-Gal antibody for the recruitment and local activation of neutrophils, monocytes and macrophages within and adjacent to wounded tissue. This is achieved by administration of compositions comprising liposomes bearing multiple α-gal epitopes (Galα1-3Galβ1-(3)4GlcNAc-R) as part of the glycolipid component. The anti-Gal antibody, which constitutes 1% of immunoglobulins in humans, apes, Old World primates and birds, interacts specifically with α-gal epitopes. In situ binding of anti-Gal to α-gal epitopes on α-gal glycolipids and to other molecules carrying this epitope, results in local activation of complement and generation of the chemotactic factors C5a, C4a and C3a. These factors direct migration of neutrophils followed by monocytes and macrophages into the injection site. These inflammatory infiltrates are suitable for combating microbes within infected wounds. In addition, the monocytes and macrophages infiltrates are contemplated to bind by their Fcγ receptors, anti-Gal antibodies via the Fc portion of anti-Gal opsonizing the α-gal liposomes, thereby and activating these cells. This in turn induces the uptake of the anti-Gal opsonized α-gal liposomes and the secretion of cytokines and growth factors that accelerate wound healing. As such treatment regimens comprising α-gal liposomes administration within and/or adjacent to a wound are contemplated to result in accelerated healing and improved repair of damaged tissues. Alternatively, topical application of ointment containing α-gal glycolipids (referred to as α-gal ointments) results in similar binding of anti-Gal to α-gal glycolipids, complement activation, chemotactic migration of neutrophils, monocytes and macrophages into the treated area, local secretion of cytokines and growth factors that contribute to accelerated wound healing.

When a wound occurs to the skin, the cells must work to close the breach and re-establish the barrier to the environment. The process of wound healing typically consists of three phases during which the injured tissue is repaired, regenerated, and new tissue is reorganized into a scar. These three phases can be classified as: a) an inflammation phase which begins on day 0 and lasts up to 3 days; b) a cellular proliferation phase from 3 to 12 days; and c) a remodeling phase from 3 days to about 6 months.

In the inflammation phase, inflammatory cells, mostly neutrophils, enter the site of the wound followed by lymphocytes, monocytes, and later macrophages. Stimulated neutrophils release proteases and reactive oxygen species into the surrounding medium, with potential adverse effects on both the adjacent tissues and the invading microorganisms. The proliferative phase consists of laying down new granulation tissue, and the formation of new blood vessels in the injured area. Fibroblasts, endothelial cells, and epithelial cells migrate to the wound site. These fibroblasts produce the collagen necessary for wound repair. In re-epithelialization, epithelial cells migrate from the free edges of the tissue across the wound. This event is succeeded by the proliferation of epithelial cells at the periphery of the wound. In general, re-epithelialization is enhanced by the presence of occlusive wound dressings that maintain a moisture barrier. Remodeling, the final phase of wound healing, is effected by both the replacement of granulation tissue with collagen and elastin fibers and the devascularization of the granulation tissue. Eventually, in most cases, a scar forms over the wounded area.

I. The Role of Inflammatory Cells in Wound Healing and Tissue Repair

Neutrophils are the first immune cells to arrive at the wound site appearing approximately 24 h after injury. They phagocytose bacteria and mediate wound debridement. Macrophages migrate into the wound 48-96 h after injury and become the predominant cells within the inflammatory response in the wound. Studies on depletion of monocytes and/or macrophages in mice by intravascular administration of specific anti-macrophage antibodies have indicated that wound healing is impaired after depletion of these cells as provided for in Leibovich et al., *Am. J. Pathol.* 78, 71 (1975), incorporated herein by reference. In contrast, depletion of granulocytes, including neutrophils, through the use of specific anti-granulocyte antibodies does not hamper the inflammatory response and subsequent wound healing and tissue repair as provided for in Leibovich et al., *Am. J. Pathol.* 78, 71 (1975), incorporated herein by reference. This result suggests that cells of the monocyte/macrophage lineage are pivotal in orchestrating wound healing and tissue repair and in remodeling following injury. As such the present invention provides compositions and methods for inducing rapid recruitment of macrophages into wounds and injured tissues to accelerate the process of wound healing and tissue repair. Circulating monocytes enter the wound and mature into macrophages and dendritic cells. They secrete interferon-γ (IFNγ), and angiogenic and fibrogenic growth factors. These factors and additional chemokines, cytokines and growth factors are produced after debridement of the injured tissue and are instrumental in the removal of dead cells, localized recruitment of fibroblasts and mesenchimal stem cells, cell proliferation and tissue remodeling to effect wound healing. This tissue repair process occurs in infected wounds, surgical incisions, burns and other traumatized tissues as disclosed in Rappolee et al., *Curr. Top. Microbiol. Immunol.* 181, 87 (1992); Nathan, *J. Clin. Invest.* 79, 319 (1987) and Singer et al., *New England Journal of Medicine* 341, 738 (1999), all of which are hereby incorporated by reference. Major chemoattractants directing migration of neutrophils, monocytes and macrophages are the C5a and C3a fragments of the complement components C5 and C3, which are generated following complement activation by antigen/antibody interactions. These chemotactic factors form a concentration gradient that guides the migration of neutrophils, monocytes and macrophages to the areas with increased concentrations of C5a and C3a.

In some embodiments, the present invention provides for compositions and methods for the recruitment and activation of large numbers of neutrophils, monocytes and macrophages into wounds by local injection of liposomes possessing multiple α-gal epitopes (Galα1-3Galβ1-4GlcNAc-R or Galα1-3Galβ1-3GlcNAc-R) on their glycolipid components, or by topical application of ointment containing α-gal glycolipids. The α-gal epitopes bind the natural anti-Gal antibody, which is the most abundant antibody in humans. This antigen/antibody interaction in turn activates complement forming the degradation products C5a and C3a that serve as effective chemoattractants for inflammatory cells.

II. Anti-Gal Antibodies and α-Gal Epitopes

Anti-Gal is an abundant natural antibody in humans constituting ~1% of all serum immunoglobulins as provided for in Galili et al., *J. Exp. Med.* 160, 1519 (1984), incorporated herein by reference. This antibody interacts specifically with the α-gal epitope (Galα1-3Galβ1-4GlcNAc-R or Galα1-3Galβ1-3GlcNAc-R) on glycolipids and glycoproteins as disclosed in Galili, *Springer Semin. Immunopath.* 15, 155 (1993), incorporated in its entirety by reference. Anti-Gal is produced throughout life as a result of antigenic stimulation by bacteria of the gastrointestinal tract as described in Galili et al., *Infect. Immun.* 56, 1730 (1988). The α-gal epitope is synthesized by the glycosylation enzyme α-1,3-galactosyltransferase (α1,3GT) and expressed in very large amounts on the cells of non-primate mammals, prosimians and in New World monkeys as provided for in Galili et al., *J. Biol. Chem.* 263, 17755 (1988), incorporated herein by reference. The α1,3GT gene was inactivated in ancestral Old World primates. Thus humans, apes, and Old World monkeys lack α-gal epitopes and produce high titer anti-Gal antibodies as provided for in Galili et al., *J. Biol. Chem.* 263, 17755 (1988), incorporated herein by reference. Anti-Gal antibodies bind in vivo to α-gal epitopes when administered to humans or Old World monkeys. This is particularly evident in the context of xenotransplantation, where the in vivo binding of anti-Gal to α-gal epitopes on transplanted pig heart or kidney is the main cause for the rapid rejection of such grafts in humans and Old World monkeys as disclosed in Galili et al., *Immunol. Today* 14, 480 (1993) and Collins et al., *J. Immunol.* 154, 5500 (1995), both of which are incorporated in their entirety by reference.

One of the main mechanisms mediating xenograft rejection is the activation of the complement cascade due to anti-Gal binding to α-gal epitopes on the endothelial cells of the xenograft. This results in the destruction of these endothelial cells by the activated complement molecules, causing collapse of the vascular bed and xenograft ischemia followed by its rapid rejection as provided for in Collins et al., *J. Immunol.* 154, 5500 (1995), hereby incorporated by reference. This in situ interaction of anti-Gal with newly introduced α-gal epitopes can be exploited for local activation of the complement system and recruitment of neutrophils, monocytes and macrophages into damaged tissues to accelerate the inflammatory response and subsequent tissue repair. Due to its ubiquitous production in humans, anti-Gal is a superior choice for this purpose.

III. Binding of Anti-Gal Antibody by α-Gal Liposome

Figure 1B:
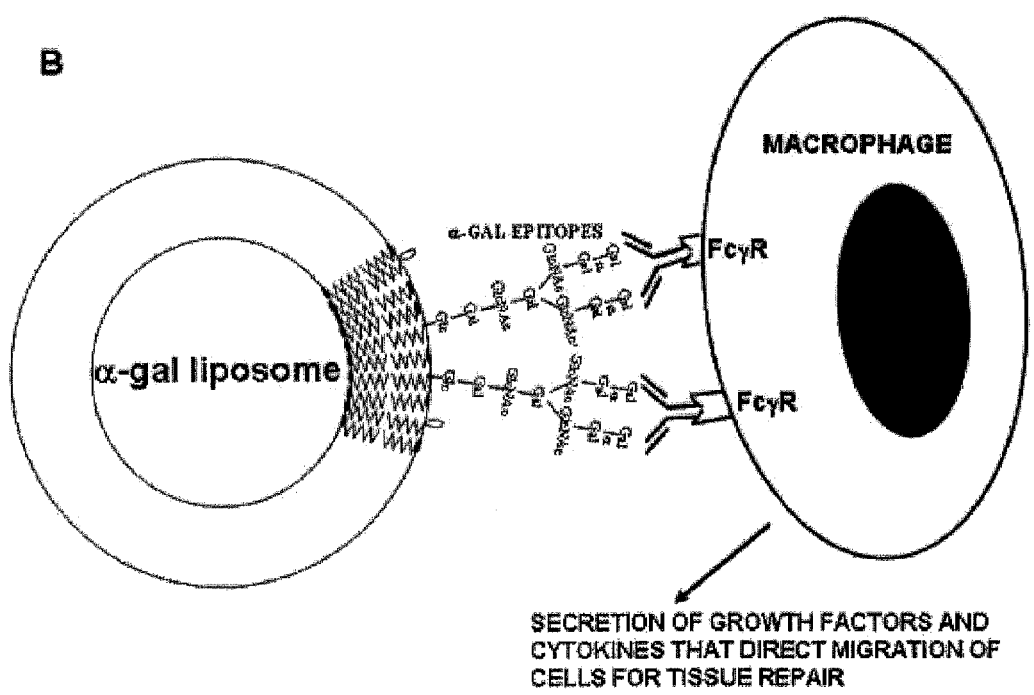
FIG. 1B illustrates an interaction between an anti-Gal coated (opsonized) α-gal liposome and a macrophage.
Figure 2A:
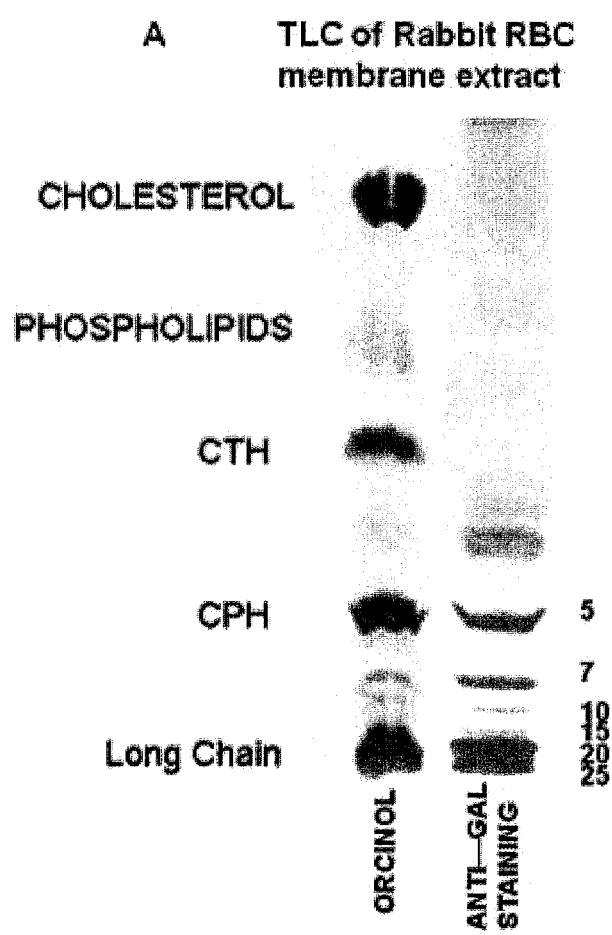
FIG. 2A depicts the separation of rabbit RBC glycolipids, phospholipids and cholesterol by thin layer chromatography (TLC), as demonstrated by nonspecific orcinol staining (left lane) and by immunostaining with an anti-Gal monoclonal antibody (mAb) designated Gal-13 (right lane) (Galili et al., J Biol Chem, 262:4683, 1987). The smallest glycolipids having three carbohydrates (ceramide tri-hexoside [CTH]) lack α-gal epitopes and thus are not stained by the anti-Gal mAb. The number of carbohydrates in each α-gal glycolipid is indicated on the right. The smallest α-gal-containing glycolipid has five carbohydrates (ceramide pentahexoside [CPH]).
Figure 2B:
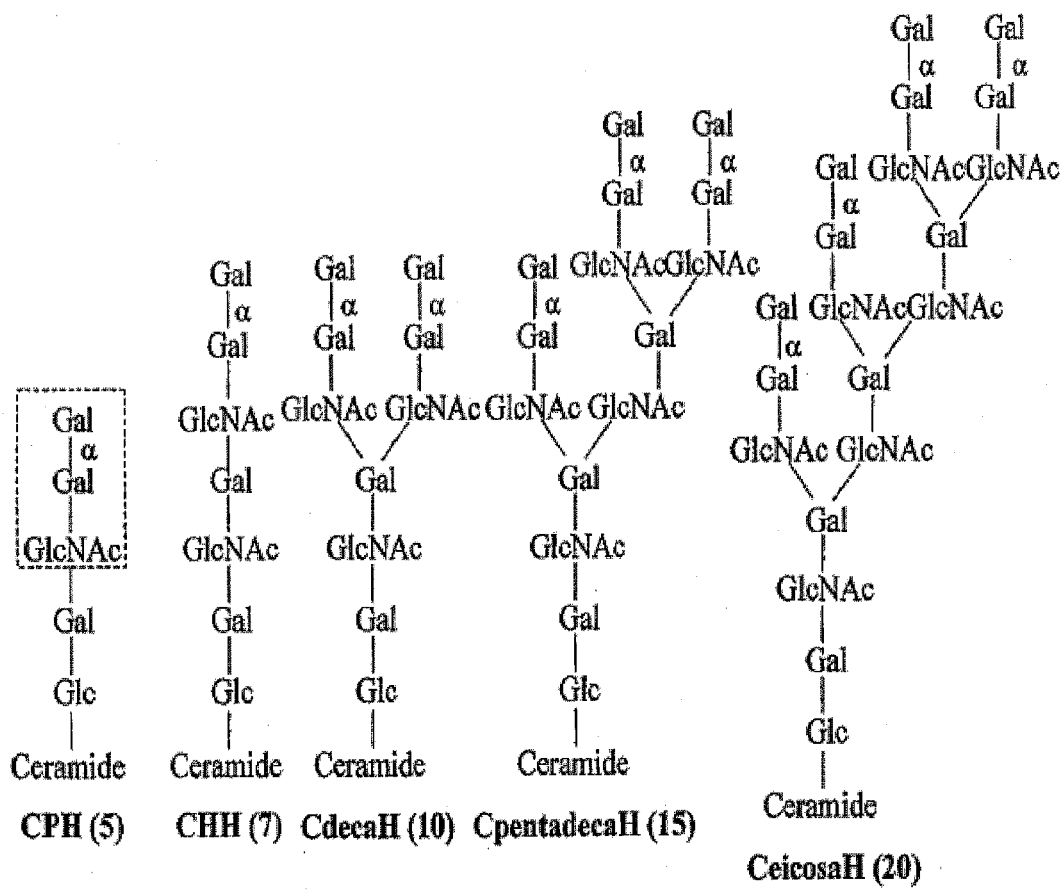
FIG. 2B provides the structures of α-gal glycolipids having five, seven, 10, 15 and 20 carbohydrates, respectively.

Recruitment of neutrophils, monocytes and macrophages into sites of infection or tissue damage is directed by a concentration gradient of fragments of activated complement molecules such as C5a, C4a and C3a. Injection of molecules or particulate material bearing α-gal epitopes is contemplated to result in local interaction between endogenous anti-Gal antibodies and the exogenous α-gal epitopes, followed by activation of the complement system. One example of particulate material carrying multiple α-gal epitopes is α-gal liposomes, which can be prepared from chloroform:methanol extracts of rabbit red blood cell (RBC) membranes as shown in FIGS. 1 and 2. These liposomes are comprised of rabbit RBC glycolipids, phospholipids and cholesterol. Since most rabbit RBC glycolipids have α-gal epitopes, these liposomes carry many of these epitopes. When the α-gal liposomes are injected intradermally or into other tissues, a high local concentration of α-gal epitopes is generated, which is available for binding to anti-Gal antibodies. Both the anti-Gal antibody and complement are contemplated to reach the injection site due to local rupture of capillaries by the injecting needle. The activation of complement and generation of C5a, C4a and C3a fragments, following anti-Gal interaction with α-gal epitopes, results in a local inflammatory reaction that induces capillary dilation, and accumulation of serum proteins at the injection site (including more anti-Gal and complement proteins). This leads to further binding of anti-Gal to the injected α-gal liposomes and activation of complement, ultimately resulting in an amplification of the inflammatory process and the increased formation of chemotactic factors for recruit of additional neutrophils, monocytes and macrophages into the injection site. Other liposomes that bear α-gal epitopes or other molecules carrying one or several α-gal epitopes are also suitable for enhancing the beneficial inflammatory response occurring at the injection site.

The monocytes/macrophages migrating into the injection site bind the anti-Gal coated (opsonized) α-gal liposomes via their Fcγ receptors (FcγR). The interaction of the Fc portion of anti-Gal (upon opsonization of α-gal liposomes) with FcγR on the monocyte and immature macrophage cell surface induces the activation of these cells and the differentiation of the monocytes into mature macrophages. Activated macrophages have been shown to secrete a variety of growth factors and cytokines including for instance: vascular endothelial cell growth factor (VGEF), epidermal growth factor (EGF), fibroblast growth factor (FGF), insulin-like growth factor (IGF), IL-1 and IL-6 as disclosed in DiPietro, *Shock* 4, 233-40 (1995); Rappolee et al., *Curr. Topics Microbial Immunol.* 181, 87-140 (1992) and Singer et al., *New England Journal of Medicine* 341, 738-46 (1999), all of which are hereby incorporated by reference.

The effect of α-gal liposomes on recruitment of macrophages and wound healing is localized to the injection site and has little to no systemic effect. The three components of the exemplary α-gal liposomes, α-gal glycolipids, phospholipids and cholesterol, are not immunogenic and therefore do not elicit a de novo immune response presumably because phospholipids and cholesterol are found in all mammalian species and because α-gal glycolipids in and of themselves do not activate T cells as disclosed in Tanemura et al., *J. Clin. Invest.* 105, 301 (2000). Accordingly, analysis of the antibody response to α-gal liposomes by ELISA (using α-gal liposomes as the solid phase antigen) revealed that antibody titers to α-gal liposomes were not elevated at 35 or 40 days post-injection. Moreover in experiments performed in anti-Gal seropositive mice, administration of α-gal liposomes did not cause abnormal behavior post-injection or increased morbidity or mortality.

Thus, injection of a preparation of α-gal liposomes in water, saline or other excipient into an infected wound, is contemplated to result in anti-Gal binding, activation of complement, generation chemotactic factors, rapid recruitment of neutrophils followed by monocytes and macrophages, phagocytosis of the infectious agent, debridement of the wound, and migration of fibroblasts into the wound. Secretion of epithelial growth factor by the activated macrophages results in epithelization, e.g. proliferation of epithelial cells to close the wound. The destruction of infectious agents and debridement of the wound by the inflammatory cell infiltrate and subsequent migration of fibroblasts and proliferation of epithelial cells is contemplated to accelerate wound healing and tissue repair.

Figure 9:
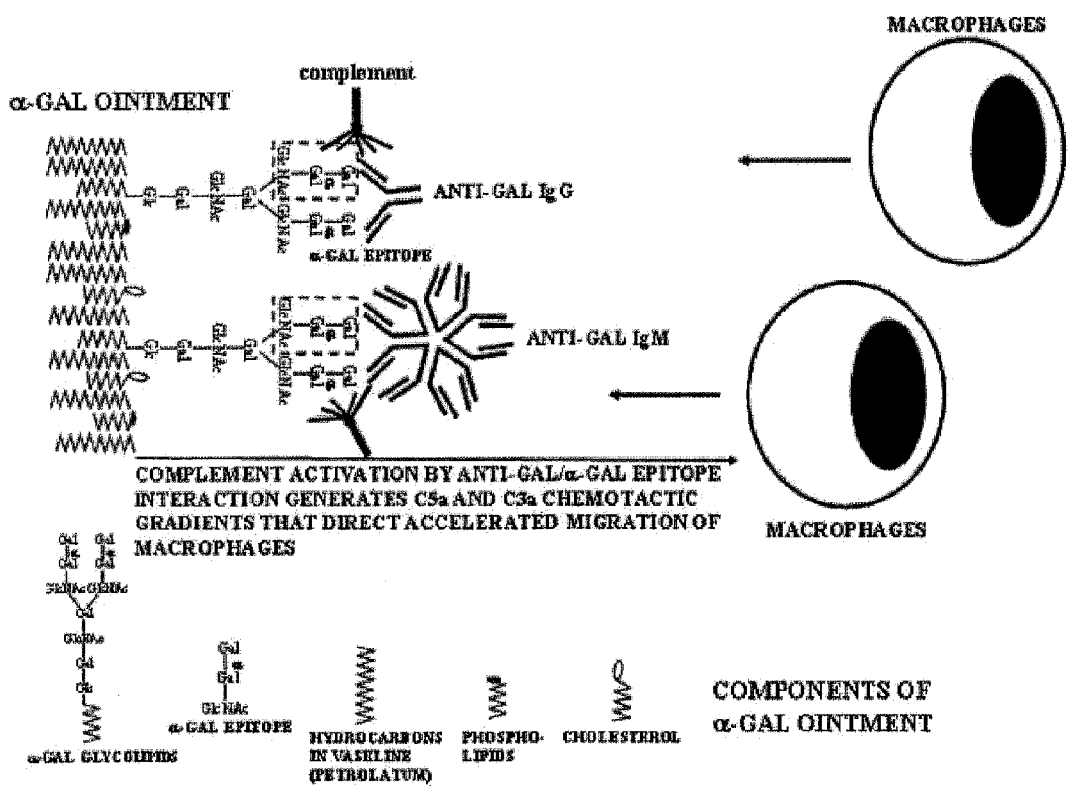
FIG. 9 illustrates one embodiment of an interaction between anti-Gal and α-gal epitopes on α-gal glycolipids applied in the form of α-gal ointment. The α-gal ointment, comprised here of a mixture of α-gal glycolipids (100 mg/ml) and petrolatum ointment (Vaseline), is applied topically on areas of damaged skin such as burns, in which serum proteins including anti-Gal and complement are released from damaged blood vessels. The α-gal epitopes (Galα1-3Galβ1-4GlcNAc-R) indicated on some of the chains in rectangles of broken lines) are present on all rabbit red cell glycolipids that carry 5 or more carbohydrate units (see FIG. 2). The present figure illustrates a representative α-gal glycolipid with 10 carbohydrate units. The fatty tail comprising the ceramide portion of the glycolipid enables mixing of the α-gal glycolipids within petrolatum (Vaseline) containing hydrocarbon chains of >25 carbons. α-Gal glycolipids within the ointment bind anti-Gal and thus, activate complement. The complement cleavage factors C5a and C3a recruit macrophages which mediate the accelerated natural process of wound healing.

A similar accelerated healing of wounds can be achieved by topical application of α-gal ointment onto injured skin areas of various wounds including burns as shown in FIG. 9. The α-gal epitopes of α-gal glycolipids within this ointment bind the anti-Gal antibody, activate complement, generate complement degradation factors C5a and C3a due to cleavage of complement molecules, recruit granulocytes, monocytes and macrophages to the treated site and thus, induce accelerated healing of the injured area.

IV. Wound Healing Applications

The compositions and methods of the present invention are suitable for treating various wounds in normal subjects and in subjects having impaired healing capabilities, such as diabetics, heart disease and/or cardiac surgical subjects, and aged subjects.

A. Surgical Incisions

In a preferred embodiment, compositions comprising α-gal liposomes are used to enhance wound healing in surgical incision sites that have been damaged as a result of ischemia. Injection of α-gal liposomes into the area surrounding the sutures and ischemic tissue enhances recruitment of neutrophils, monocytes and macrophages into the surgical incision site ultimately resulting in improved wound healing. In this way, the present invention is suitable for shortening the time required for healing of wounds and repair of damaged tissues following surgery. A specific non-limiting example is the removal of a colon carcinoma and reconnection of the colon wall at the site of tumor resection.

B. Cardiac Tissue

In another embodiment, compositions comprising α-gal liposomes are used to treat tissue. While not limiting the scope of the invention in any way, one example contemplated by the invention is the treatment of skeletal muscle damaged due to physical trauma or heart muscle damaged due to ischemia. Injection of α-gal liposomes into the injured or damaged muscle tissue enhances recruitment of neutrophils, monocytes and macrophages into the injured muscle ultimately resulting in improved tissue repair. In particular the inflammatory cell infiltrate recruits myoblasts, which subsequently differentiate into functional cardiac myocytes in treated heart muscle, or fuse and differentiate into functional skeletal muscle fibers in treated skeletal muscle. In this way the biomechanical function of the damaged muscle is restored.

In preferred embodiments, the compositions and methods of the present invention are used to promote healing due to cardiac tissue damage in both normal subjects and in subjects having impaired healing capabilities. For example, the heart is comprised of cardiac tissue. This tissue may be damaged or otherwise compromised during cardiac trauma, disease or related events including but not limited to cardiac surgery, coronary heart disease, cardiomyopathy, cardiovascular disease, ischemic heart disease, heart failure, hypertensive heart disease, inflammatory heart disease and valvular heart disease. Mortality rates for cardiac surgical procedures continue to be a cause for concern. For example, repairs of congenital heart defects are currently estimated to have 4-6% mortality rates. One non-limiting example of wounds that may receive benefit from the compositions and methods of the present invention are infected deep sternum incisions that are observed in an appreciable number of open-heart surgery patients. Injection of α-gal glycolipid preparations (e.g., α-gal liposomes) into the infected area of the sternum enhances recruitment of neutrophils, monocytes and macrophages into the surgical incision site ultimately resulting in improved wound healing.

In another embodiment α-gal liposomes are injected into cardiac muscle injured by ischemia. These injected α-gal liposomes bind in situ the endogenous natural anti-Gal antibody. This antigen/antibody interaction of α-gal liposomes/anti-Gal results in local activation of the complement system and generation of the chemotactic cleavage complement peptides C5a, C4a and C3a. These chemotactic factors direct the migration of macrophages into the injection site. Some of the macrophages have the potential of becoming stem cells. The macrophages further bind the anti-Gal coated α-gal liposomes via their Fcγ receptors (FcγR) are activated by this interaction. This activation results in the secretion of a variety of cytokines growth factors. The activated macrophages induce local angiogenesis and generate a microenvironment that may be conducive to the recruitment of stem cells from adjacent uninjured myocardium or from other sites in the body. Stem cells recruited by the α-gal liposomes treatment receive instructive cues from uninjured cardiomyocytes, from the cytoskeleton of the heart muscle and from the microenvironment within the heart muscle and develop into cardiomyocytes that repopulate the injured myocardium. Ultimately the treatment with α-gal liposomes injected into the injured heart muscle result in repair and regeneration of the heart muscle and restoration of the heart muscle function.

C. Nerve Tissue

Moreover, injection of α-gal liposomes into nerves damaged by physical or other trauma, or because of nerve degeneration, enhances recruitment of neutrophils, monocytes and macrophages. The activated macrophages debride the damaged nerve tissue and secrete nerve growth factors that induce axonal regeneration and restoration of nerve pulse conductivity via the regenerating nerve. This is contemplated to result in partial or complete restoration of function of the treated nerve.

In one embodiment, the present invention contemplates compositions and methods to recruit stem cells, for healing and/or repairing damaged or injured brain tissue. In one embodiment, α-gal liposomes are injected intracranially into injured brain areas. In one embodiment, the brain is a human brain. In one embodiment, the brain injury comprises damage including, but not limited to, that following ischemic infarction. In one embodiment, the α-gal liposomes are injected at any volume that is suitable for injection into the injured brain tissue and at a concentration ranging between 0.01 and 500 mg/ml. Although it is not necessary to understand the mechanism of an invention, it is believed that the interaction between the injected α-gal liposomes and the anti-Gal antibody activates complement and the generated chemotactic complement cleavage peptides recruit monocytes and macrophages to the injection site. The macrophages are activated by Fc/FcγR interaction with anti-Gal coated α-gal liposomes and secrete cytokines and growth factors that promote healing of the injured brain tissue and recruit stem cells. These stem cells proliferate and differentiate in to brain cells that repair and regenerate the injured brain tissue.

D. Burns

In further embodiments, compositions comprising α-gal glycolipids and/or α-gal epitopes are applied to skin burns. Their interaction with the anti-Gal antibody, leaking to the burn surface together with other serum proteins, results in complement activation recruitment of neutrophils, monocytes and macrophages and ultimately resulting in accelerated healing of the burn.

E. Diabetes

In an additional embodiment, the disclosed α-gal liposome can be combined in compositions with at least one anti-Gal antibody. The mixture of these antigen and antibody will result in increased recruitment of neutrophils, monocytes and macrophages to the injured area. Such treatment is ideal, for example, for aged individuals or subjects with advanced diabetes patients where poor vascularization prevents sufficient anti-Gal antibody from reaching injured areas. Alternatively, such treatment may be applicable to non-primate mammals lacking the anti-Gal antibody. The applied immune complexes activate complement and thus accelerate wound healing.

In some embodiments, the local anti-Gal mediated activation of complement and subsequent recruitment of activated macrophages into an injection site is achieved by employing a variety of natural or synthetic macromolecules carrying multiple α-gal epitopes. Various commercially available glycolipids (Dextra Laboratories, Ltd., United Kingdom) are suitable for use in the compositions and methods of the present invention for generation of α-gal liposomes. These glycolipids include but are not limited to: i) Galα-3Gal glycolipids: α1-3 galactobiose (G203); linear B-2 trisaccharide (GN334); and Galili pentasaccharide (L537). Various other glycoconjugates with α-gal epitopes available from Dextra include for instance: Galα1-3Galβ1-4Glc-BSA (NGP0330); Galα1-3Galβ1-4(3-deoxyGlcNAc)-HAS (NGP2335); Galα1-3Galβ1-4GlcNAcβ1-HDPE (NGL0334); and Galα1-3Gal-BSA (NGP0203). Several non-limiting examples of additional macromolecules with α-gal epitopes that are suitable for injection and subsequent in situ binding to anti-Gal antibodies and local activation of complement include: mouse laminin with 50-70 α-gal epitopes as disclosed in Galili, *Springer Seminars in Immunopathology* 15, 155 (1993), incorporated herein by reference; multiple synthetic α-gal epitopes linked to BSA as disclosed in Stone et al., *Transplantation* 83, 201 (2007), hereby incorporated by reference; GAS914 produced commercially by Novartis and disclosed in Zhong et al., *Transplantation* 75, 10 (2003), incorporated herein by reference; the α-gal polyethylene glycol conjugate TPC as disclosed in Schirmer et al., *Xenotransplantation* 11, 436 (2004), hereby incorporated by reference, and α-gal epitope-mimicking peptides linked to a macromolecule backbone as disclosed in Sandrin et al., *Glycoconj. J.* 14, 97 (1997), hereby incorporated by reference. Injection or topical application of such macromolecules results in local interaction with the pre-formed anti-Gal antibody present in all humans, activation of complement, recruitment of inflammatory cells into the injection site and differentiation of these cells thereby effecting improvements in the duration and quality of wound healing.

In still further embodiments a glycoprotein carrier such as the human alpha1-acid glycoprotein (α1-AG) is utilized. α1-AG is abundant in human serum, non-immunogenic in humans, and can be obtained commercially in purified form. α1-AG is a small glycoprotein (e.g., 40 kDa) with five N-linked carbohydrate chains, each with 2 or more antennae with the terminal structure sialic acid-Galβ1-4GlcNAc-R as disclosed in Schmid et al., *Biochemistry* 13, 2694-2697 (1973), incorporated herein by reference. To synthesize the α-gal epitopes on the α1-AG the sialic acid is first removed to expose the penultimate N-acetyllactosamine (Galβ1-4GlcNAc-R). Next the appropriate carbohydrate is added to this backbone to synthesize the α-gal epitope. Briefly, neuraminidase is used to remove the terminal sialic acid, followed by the addition of an α1-3Gal unit using a galactosyltransferase (e.g., recombinant α1,3 galactosyltransferase) and uridine diphosphate-galactose as the sugar donor as disclosed in Galili, *Cancer Immunol. Immunother.* 53, 935-945 (2004), hereby incorporated by reference.

F. Osteoarthritis (OA)

In preferred embodiments, the methods and compositions of the present invention are used to reduce the symptoms associated with osteoarthritis (OA), a disease that may also be referred to as degenerative arthritis. Traditionally, treatment for osteoarthritis is limited to pain relievers including but not limited to non-steroidal anti-inflammatory drugs (NSAIDS), corticosteroids, COX-2 selective inhibitors and topical creams. In more severe cases of OA the subject receives either injections of local anesthetics such as lidocaine or undergoes joint replacement surgery for the affected area. In a further embodiment, injection of α-gal liposomes into the synovial cavity, or into damaged cartilage within injured bones enhances recruitment of neutrophils, monocytes and macrophages into the synovial cavity or cartilage ultimately resulting in tissue repair. In particular, macrophages activated by the binding of α-gal liposome/anti-Gal antibody complexes mediate debridement of the damaged cartilage and through secretion of growth factors and cytokines direct migration of chondroblasts into the damaged cartilage. The chondroblasts in turn secrete collagen and other cartilage matrix proteins and polysaccharides, resulting in repair and remodeling of the damaged articular or meniscus cartilage within the treated joint. Similarly, macrophages activated by the binding of α-gal liposome/anti-Gal antibody complexes mediate debridement of the damaged bone and through secretion of growth factors and cytokines recruit osteoclasts and osteoblasts into the injection site for repair and remodeling of the damaged bone.

In a further embodiment, injection of α-gal liposomes into the synovial cavity, or into damaged cartilage within injured bones enhances recruitment of neutrophils, monocytes and macrophages into the synovial cavity or cartilage ultimately resulting in tissue repair. In particular, macrophages activated by the binding of α-gal liposome/anti-Gal antibody complexes mediate debridement of the damaged cartilage and through secretion of growth factors and cytokines direct migration of chondroblasts into the damaged cartilage. The chondroblasts in turn secrete collagen and other cartilage matrix proteins and polysaccharides, resulting in repair and remodeling of the damaged articular or meniscus cartilage within the treated joint. Similarly, macrophages activated by the binding of α-gal liposome/anti-Gal antibody complexes mediate debridement of the damaged bone and through secretion of growth factors and cytokines recruit osteoclasts and osteoblasts into the injection site for repair and remodeling of the damaged bone.

G. Diabetes

In preferred embodiments, the present invention is used to promote healing in tissue damage as a result of diabetes in both normal subjects and in subjects having impaired healing capabilities. Diabetes can cause many complications, including but in no way limited to acute complications such as hypoglycemia, ketoacidosis, or non-ketotic hyperosmolar coma, long-term complications including but not limited to cardiovascular disease, chronic renal failure, retinal damage, blindness, nerve damage and microvascular damage. Poor healing of many superficial wounds due to diabetes can lead to many diseases including but not limited to gangrene, which may require amputation. In the developed world, diabetes is the most significant cause of adult blindness in the non-elderly and the leading cause of non-traumatic amputation in adults, and diabetic nephropathy is the main illness requiring renal dialysis in the United States. The α-gal liposomes of the present invention may be preferably used in wound care devices in patients with diabetes, in order to induce effective wound healing by local activation of complement as a result of anti-Gal antibody binding to α-gal liposomes. In still another embodiment, the invention relates to the use of α-gal liposomes in wound care devices applied to a wound in a subject following either diabetic complications or the natural progression of the disease.

In another embodiment, α-gal liposomes are used for injection into the pancreas in diabetic patients, in order to restore the formation of Langerhans Islets in the pancreas. These islets contain cells that secrete insulin. Injection of α-gal liposomes at a concentration ranging between 0.01 and 500 mg/ml. The injection is performed by ultrasound endoscopy, or by laparoscopy, or any other type of injection, into the pancreas tissue of diabetic patients induces the recruitment and activation of macrophages that promote tissue repair. Some of these macrophages have stem cell potential and can differentiate into Langerhans Islet cells. In addition, the activated macrophages secrete cytokines and growth factors that promote recruitment of stem cells which give rise within the pancreas to formation of Langerhans Islets, which secrete several hormones and include, but are not limited to, insulin.

For example, in some patients with Type I diabetes and in some of the patients with Type II diabetes the Langerhans Islets have been destroyed. In one embodiment, the present invention contemplates restoring biologically active Langerhans Islets in the pancreas of these patients. It is believed that such restoration would thereby provide endogenous insulin and cure the state of diabetes. In one embodiment, α-gal liposomes at a concentration ranging between 0.01 and 500 mg/ml are injected into the pancreas by a device enabling endoscopy ultrasound, or by laparoscopy, or by any other procedure which enables for direct injection of the α-gal liposomes into the pancreas. The interaction between the injected α-gal liposomes and the anti-Gal antibody activates complement and the generated chemotactic complement cleavage peptides recruit monocytes and macrophages to the injection site. The macrophages are activated by Fc/FcγR interaction with anti-Gal coated α-gal liposomes and secrete cytokines and growth factors that recruit stem cells. These stem cells and/or stem cells originating from macrophages proliferate and differentiate into Langerhans Islet cells that form the islets and secrete endogenous insulin.

H. Nerve System

In some embodiments, the methods and compositions of the present invention are used to restore structure and/or function to injured tissues of the central and peripheral nerve system. In one embodiment, the present invention contemplates treating brain tissue that is injured as a result of conditions including, but not limited to, ischemia (i.e., for example, infarct), or trauma. Although it is not necessary to understand the mechanism of an invention, it is believed that injection of α-gal liposomes into the injured brain tissue promotes recruitment and activation of macrophages which transdifferentiate into neurons and/or recruit and activate stem cells. It is also believed that the activated macrophages secrete cytokines and growth factors that may promote repair of the injured brain tissue. α-gal liposomes recruits and induces stem cell migration from adjacent uninjured brain tissue, or from other site in the body, or are the result of transdifferentiation from macrophages to the injured brain tissue. These stem cells are believed to differentiate into brain cells that replace the injured tissue, based on cues from normal brain cells, matrix and microenvironment. Ultimately, α-gal liposomes injection into the injured brain tissue restores partially or completely the structure and function of the treated tissue.

In another embodiment, injection of α-gal liposomes into nerves damaged by physical trauma, or by other types of trauma, or because of nerve degeneration, enhances recruitment of neutrophils, monocytes and macrophages into the injured area of the nerve. The activated macrophages debride the damaged nerve tissue and secrete nerve growth factors that recruit stem cells and induce axonal regeneration and restoration of nerve pulse conductivity via the regenerating nerve. This is contemplated to result in partial or complete restoration of function of the treated nerve.

I. Musculoskeletal

In preferred embodiments the methods and compositions of the present invention are used to restore structure and function injured parts of the musculoskeletal system. In one embodiment the present invention can be used to treat skeletal muscle injured due to physical trauma or to ischemia. Injection of α-gal liposomes into the injured muscle tissue enhances recruitment of neutrophils, monocytes and macrophages into the injured muscle. The recruited macrophages are activated by Fc/FcγR interaction with anti-Gal coated α-gal liposomes and secrete cytokines and growth factors that promote repair of the injured muscle tissue, by recruiting stem cells. A proportion of the macrophages also has the potential of stem cells. The stem cells recruited by macrophages or originating from macrophages differentiate into myoblasts that fuse into myotubes which repair the injured muscle and restore its biological activity.

In a further embodiment, injection of α-gal liposomes into the synovial cavity, or into damaged cartilage in joints enhances recruitment of neutrophils, monocytes and macrophages into the synovial cavity or cartilage ultimately resulting in tissue repair. In particular, macrophages activated by the binding of α-gal liposome/anti-Gal antibody complexes mediate debridement of the damaged cartilage and through secretion of growth factors and cytokines direct migration of stem cells that differentiate into chondroblasts within the damaged cartilage. The chondroblasts in turn secrete collagen and other cartilage matrix proteins, polysaccharides and proteoglycans, resulting in repair and regeneration of the damaged articular or meniscus cartilage within the treated joint. Similarly, macrophages activated by the binding of α-gal liposome/anti-Gal antibody complexes mediate debridement of the damaged bone and through secretion of growth factors and cytokines recruit osteoclasts and osteoblasts into the injection site for repair and regeneration of the damaged bone.

J. Vascular System

In some embodiments, the present invention contemplates compositions and methods for the recruitment of stem cells, resulting in repair and regeneration of the blood vessel wall. For example, α-gal liposomes may be administered to patients with damaged blood vessels or having an anastomoses. In one embodiment, the injured blood vessel may be surrounded by a wound care device containing α-gal liposomes at a concentration ranging between 0.01 and 500 mg/ml. This device can be in the form of a gel, plasma clot or fibrin clot surrounding part or the whole injured blood vessel. Alternatively, a collagen sheet or any biodegradable or non-biodegradable sheet containing the α-gal liposomes or having on its surface α-gal liposomes and which can be shaped into a tube around the injured blood vessel can be used to apply α-gal liposomes around the injured blood vessel. Although it is not necessary to understand the mechanism of an invention, it is believed that the interaction between the injected α-gal liposomes and the anti-Gal antibody activates complement and the generated chemotactic complement cleavage peptides recruit monocytes and macrophages to the injection site. The macrophages are activated by Fc/FcγR interaction with anti-Gal coated α-gal liposomes and secrete cytokines and growth factors that promote the repair of the injured blood vessel wall. These secreted cytokines and growth factors also recruit stem cells that proliferate and differentiate into cells that enable the regeneration of the intact blood vessel wall. Some of the recruited macrophages, which have stem cell potential, also may trans-differentiate into cells that repair the injured blood vessel.

K. Gastrointestinal System

In one embodiment, the present invention contemplates compositions and methods for recruiting stem cells, resulting in repair and regeneration of the gastrointestinal wall. In one embodiment, the patient comprises an ulcer and/or other injuries to the gastrointestinal tract. The treatment methods described herein are applicable to any damage to the wall at any part of the gastrointestinal tract. In one embodiment, an injured gastrointestinal area may be injected with α-gal liposomes at a concentration ranging between 0.01 and 500 mg/ml. Although it is not necessary to understand the mechanism of an invention, it is believed that the interaction between the injected α-gal liposomes and the anti-Gal antibody activates complement and the generated chemotactic complement cleavage peptides recruit monocytes and macrophages to the injection site. The macrophages are activated by Fc/FcγR interaction with anti-Gal coated α-gal liposomes and secrete cytokines and growth factors that recruit stem cells and promote the repair of the injured tissue. The recruited stem cells proliferate and differentiate into cells that replace the injured cells and repair the damaged gastrointestinal wall at the injection site.

V. Wound Care Devices

In some embodiments, the invention relates to the use of α-gal liposomes in wound care devices for aged subjects in order to induce effective wound healing by local activation of complement as a result of anti-Gal antibody binding to α-gal lipososmes. In still another embodiment, the invention relates to the use of α-gal liposomes in wound care devices applied to a wound in a subject following trauma. While not limiting the scope of the present invention, one example of a use for the present invention is the treatment of a subject recovering from a car accident resulting in injuries to said subject.

In one embodiment, a wound care device comprises an injury care device selected from the group consisting of syringes, adhesive bands, compression bandages, sponges, gels, semi-permeable films, plasma clots, fibrin clots. In one embodiment, the device comprises physiological compositions including, but not limited to, solutions, suspensions, emulsions, creams, ointments, aerosol sprays, collagen containing substances, stabilizers, drops, matrix-forming substances, foams and/or dried preparation.

VI. Pharmaceutical Compositions

The present invention further contemplates pharmaceutical compositions capable of: i) delivering α-gal epitopes; or ii) administering compositions that interact with α-gal epitopes. The pharmaceutical compositions of the present invention may be administered in a number of ways depending upon whether local or systemic treatment is desired and upon the area to be treated. Administration may be topical, pulmonary (e.g., by inhalation or insufflation of powders or aerosols, including by nebulizer; intratracheal, intranasal, epidermal and transdermal), oral, and/or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 µg to 100 g per kg of body weight, once or more daily, to once every 20 years.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: kDa (kilodalton); rec. (recombinant); N (normal); M (molar); mM (millimolar); µM (micromolar); mol (moles); mmol (millimoles); µmol (micromoles); nmol (nanomoles); pmol (picomoles); g (grams); mg (milligrams); µm (micrograms); ng (nanograms); 1 or L (liters); ml (milliliters); µl (microliters); cm (centimeters); mm (millimeters); µm (micrometers); nm (nanometers); C (degrees Centigrade); α1,3GT (α1,3 galactosyltransferase); BSA (bovine serum albumin); ELISA (enzyme linked immunosorbent assay); HRP (horseradish peroxidase) IFNγ (interferon-γ); knockout (KO); mAb (monoclonal antibody); OD (optical density); OPD (ortho phenylene diamine); PBS (phosphate buffered saline); RBC (rabbit red blood cells);

Example 1

Production of α-Gal Liposomes and Binding of Anti-Gal

Exemplary α-gal liposomes are generated from extracts of rabbit red blood cell (RBC) membranes. These membranes are used since they contain glycolipids carrying from one to more than seven α-gal epitopes per molecule as disclosed in Eto et al., *Biochem.* (*Tokyo*) 64, 205, (1968); Stellner et al., *Arch. Biochem. Biophys.* 133, 464 (1973); Dabrowski et al., *J. Biol. Chem.* 259, 7648 (1984) and Hanfland et al., *Carbohydr. Res.* 178, 1 (1988), all of which are hereby incorporated by reference. However, α-gal liposomes may be produced from any natural or synthetic source of α-gal glycolipids upon addition of phospholipids in the presence or absence of cholesterol, after processing as described herein. As a non-limiting example, rabbit RBC are used at a volume of 0.25 liter packed cells. The RBC are lysed by repeated washes with distilled water. The rabbit RBC membranes are then mixed with a solution of 600 ml chloroform and 900 ml methanol for 20 h with constant stirring to dissolve the membrane glycolipids, phospholipids and cholesterol into the extracting solution. In contrast, proteins are denatured and are precipitating within and upon the membranes. Subsequently, the mixture is filtered to remove non-solubilized fragments and denatured proteins. The extract contains the rabbit RBC phospholipids, cholesterol and glycolipids, dissolved in the organic solution of chloroform and methanol (FIG. 2A). With the exception of the glycolipid ceramide tri-hexoside (CTH) having the structure Galα1-4Galβ1-4Glc-Cer, the glycolipids extracted from rabbit RBC membranes generally have 5 to more than 25 carbohydrate units in their carbohydrate chains with one or several branches, all of which are capped with α-gal epitopes. Rabbit RBC glycolipids were also reported to have 30, 35 and even 40 carbohydrate units with α-gal epitopes on their branched carbohydrate chains as provided for in Honma et al., *J. Biochem.* (*Tokyo*) 90, 1187 (1981), incorporated in its entirety by reference. The extract containing glycolipids, phospholipids and cholesterol is subsequently dried in a rotary evaporator. The amount of dried extract is approximately 300 mg per 0.25 liter of packed rabbit RBC.

Thirty ml of saline is added to the dried extract, which is then subjected to sonication in a sonication bath. This sonication process results in conversion of the extract into liposomes comprised of α-gal glycolipids, phospholipids and cholesterol, as schematically illustrated in FIG. 1A. The α-gal liposomes have a size in the range of 0.1-20 μm, with the average size controlled by the length and intensity of the sonication process. Because the α-gal epitopes of many of the α-gal glycolipids protrude out of the liposomes, these epitopes readily interact with anti-Gal antibodies. This interaction results in activation of the complement cascade by anti-Gal binding to α-gal liposomes and the generation of C5a and C3a complement fragments, which in turn, form a chemotactic gradient that directs the migration of neutrophils, monocytes and macrophages from the circulation and from the peri-vascular space into the site of the α-gal liposome depot. The inflammatory cell infiltrate is readily observed in the histological sections of FIG. 6. The neutrophils and macrophages are capable of destroying microbial agents such as bacteria, viruses or fungi in the region of the injected α-gal liposomes. Macrophages have Fcγ receptors (FcγR) that bind to the Fc portion of IgG molecules that have bound to antigen. In this way, anti-Gal IgG molecules that bind to α-gal epitopes on the α-gal liposomes, also bind to FcγR on the recruited macrophages, as schematically illustrated in FIG. 1B. This interaction results in activation of the macrophage, internalization of the α-gal liposomes and secretion of a wide variety of growth factors, cytokines and chemokines to orchestrate the healing and remodeling of damaged tissue in part by recruiting fibroblasts and mesenchimal stem cells and stimulate proliferation of epithelial cells.

Figure 3A:
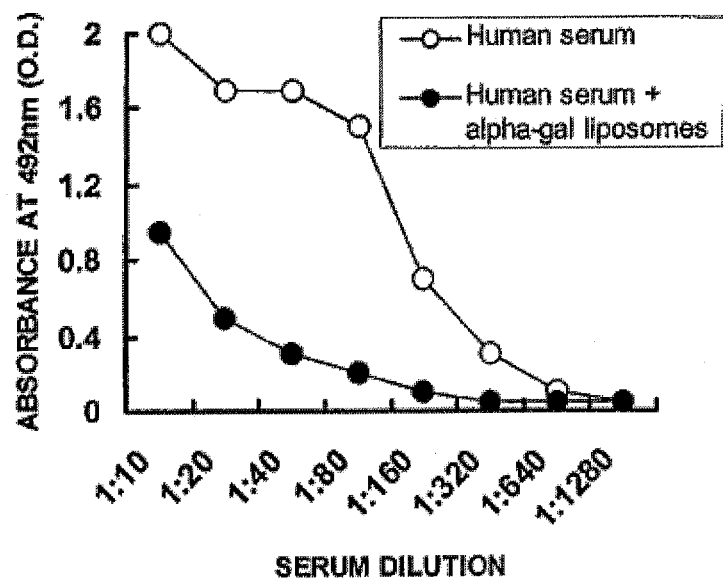
FIG. 3A shows a graph of the binding of anti-Gal to α-gal liposomes in suspension as demonstrated by neutralization of anti-Gal in human serum. Serum was incubated with 10 mg/ml α-gal liposomes for 2 h at 37° C. Subsequently, the serum was placed in ELISA wells (in serial two-fold dilutions starting at a serum dilution of 1:10) coated with synthetic α-gal epitopes linked to bovine serum albumin (α-gal BSA) as the solid-phase antigen. The anti-Gal within the serum that was not neutralized by the α-gal liposomes bound to the α-gal BSA-coated wells. Binding of anti-Gal to α-gal BSA was determined by the subsequent binding of rabbit anti-human IgG coupled to horseradish peroxidase (HRP) and color development with O-phenylene diamine (OPD). Human serum incubated in the presence (●) or absence (○) of α-gal liposomes is shown.

The specific binding of anti-Gal of human and mouse origin to the exemplary α-gal liposomes is graphically depicted in FIG. 3. Specifically, FIG. 3A shows the binding of anti-Gal to α-gal liposomes in suspension. When tested for binding to synthetic α-gal epitopes linked to bovine serum albumin (α-gal BSA) as solid-phase antigen, binding at a level higher than 1.0 optical density (OD) could be observed at serum dilutions of up to 1:80. However, if the serum was pre-incubated for 2 h at 37° C. with 10 mg/ml of α-gal liposomes, subsequent binding to the solid-phase α-gal BSA was less than 1.0 OD even at the lowest serum dilution of 1:10. This indicates that much of the serum anti-Gal binds to α-gal liposomes in suspension and therefore it is neutralized and is unavailable for the subsequent binding to the α-gal BSA as solid-phase antigen in the ELISA.

Figure 3B:
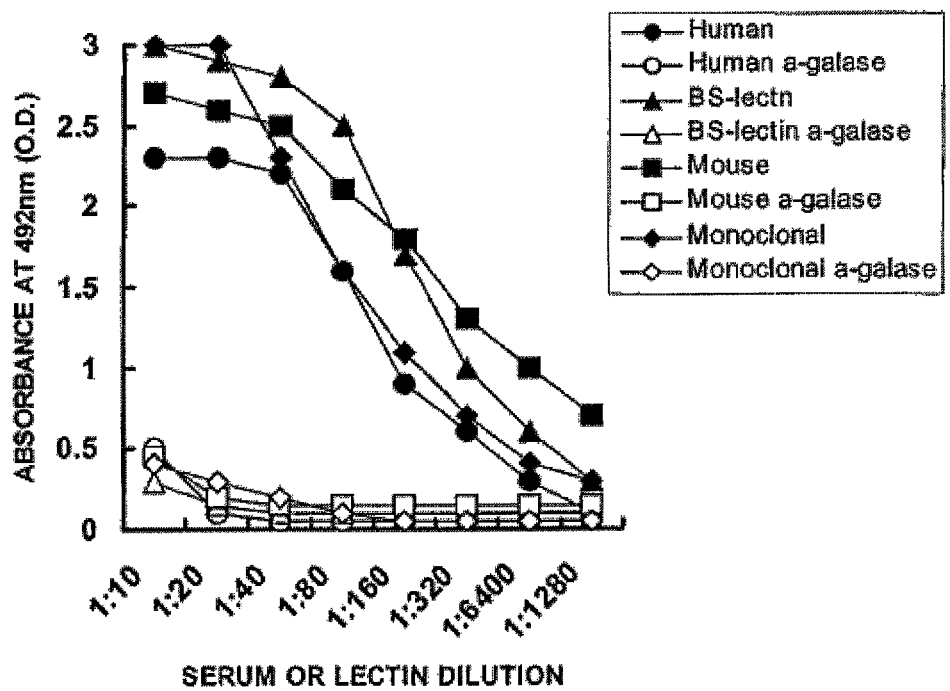
FIG. 3B shows a graph of the binding of serum anti-Gal to α-gal liposomes as solid-phase antigen. α-Gal liposomes (100 µg/ml) in phosphate buffered saline (PBS) were dried in ELISA wells. After blocking with 1% BSA in PBS, the α-gal epitopes on α-gal liposomes in control wells were specifically removed from the glycolipids carbohydrate chains by incubation for 1 h at 37° C. with 10 units/ml recombinant α-galactosidase (α-galase). Anti-Gal readily binds to α-gal epitopes on the α-gal liposomes, and is evident even at a serum dilution of 1:320 (●). Elimination of the terminal α-galactosyl unit by α-galactosidase results in complete elimination of the binding even at a serum dilution of 1:20 (○). Anti-Gal binding was evident in KO mouse serum dilution of 1:1280 (■), whereas treatment of α-gal liposomes with α-galactosidase resulted in elimination of >99% of anti-Gal binding (□). Similarly, the anti-Gal monoclonal antibody (mAb) M86 bound effectively to the α-gal liposomes (♦). No significant binding was observed in wells treated with α-galactosidase (◇). The lectin Bandeiraea simplicifolia IB4 (BS lectin with starting concentration of 10 µg/ml) that binds specifically to α-gal epitopes was observed to bind to α-gal liposomes (▲), but not to these liposomes after they were treated with α-galactosidase (△).

Similarly FIG. 3B shows the binding of human and mouse anti-Gal to α-gal liposomes that serve as a solid-phase antigen in an ELISA. The α-gal liposomes were plated as 50 μl aliquots of a 100 μg/ml suspension in phosphate buffered saline (PBS) in ELISA wells and dried overnight. The drying results in the firm adhesion of the α-gal liposomes to the wells. The wells were subsequently blocked with 1% BSA in PBS. Human serum, α1,3galactosyltransferase (α1,3GT) knockout (KO) mouse serum containing anti-Gal antibody, and mouse monoclonal anti-Gal as disclosed in Galili et al., *Transplantation* 65, 1129 (1998), hereby incorporated by reference, were added to the wells. The α1,3GT KO mouse serum contains anti-Gal antibodies upon immunization of the mouse with pig kidney membranes as provided for in Tanemura et al., *J. Clin. Invest.* 105, 301 (2000), hereby incorporated by reference. After 2 h incubation, the wells were washed and binding of anti-Gal to α-gal liposomes was determined by the addition of the corresponding horseradish peroxidase (HRP) coupled anti-human, or anti-mouse secondary antibody followed by color reaction with ortho phenylene diamine (OPD). Anti-Gal readily binds to α-gal liposomes, with 1.0 OD value at a serum dilution of 1:160 (●). The specificity of the anti-Gal/α-gal liposome interaction was demonstrated be eliminating anti-Gal binding, upon treatment of the α-gal liposomes coating the ELISA wells with recombinant α-galactosidase as disclosed in Stone et al., *Transplantation* 83, 201 (2007), incorporated herein by reference (○). The α-galactosidase enzyme cleaves the terminal galactose unit from the α-gal epitope, thereby destroying this epitope. Following such enzymatic treatment, the binding of anti-Gal to the liposomes could not be detected. The anti-Gal specific binding to α-gal liposomes was also demonstrated using serum from immunized KO mice (■), whereas treatment of the α-gal liposomes with α-galactosidase eliminated anti-Gal binding (□). Specific binding of α-gal epitopes by α-gal liposomes was also observed using an anti-Gal mAb from hybridoma cell supernatants (◆). As expected, the anti-Gal mAb did not bind to α-gal liposomes after treatment with α-galactosidase (◇). Similar specific binding to α-gal liposomes was observed with the α-gal epitope reactive lectin *Bandeiraea simplicifolia* IB4 (BS lectin) (▲) as provided for in Wood et al., *Arch. Biochem. Biophys.* 198, 1 (1979), incorporated herein by reference. The binding of this lectin was also abolished by treatment with α-galactosidase (Δ). These observations clearly demonstrate that the α-gal liposomes produced by sonication of chloroform/methanol extracts from rabbit RBC membranes, readily bind to anti-Gal antibodies. Although it is not necessary to understand the mechanism of an invention, it is believed that binding of anti-Gal to α-gal liposomes occurs in vivo at the injection site in subjects possessing anti-Gal antibodies.

Example 2

Binding of Anti-Gal to α-Gal Liposomes Induces Complement Activation

Figure 4A:
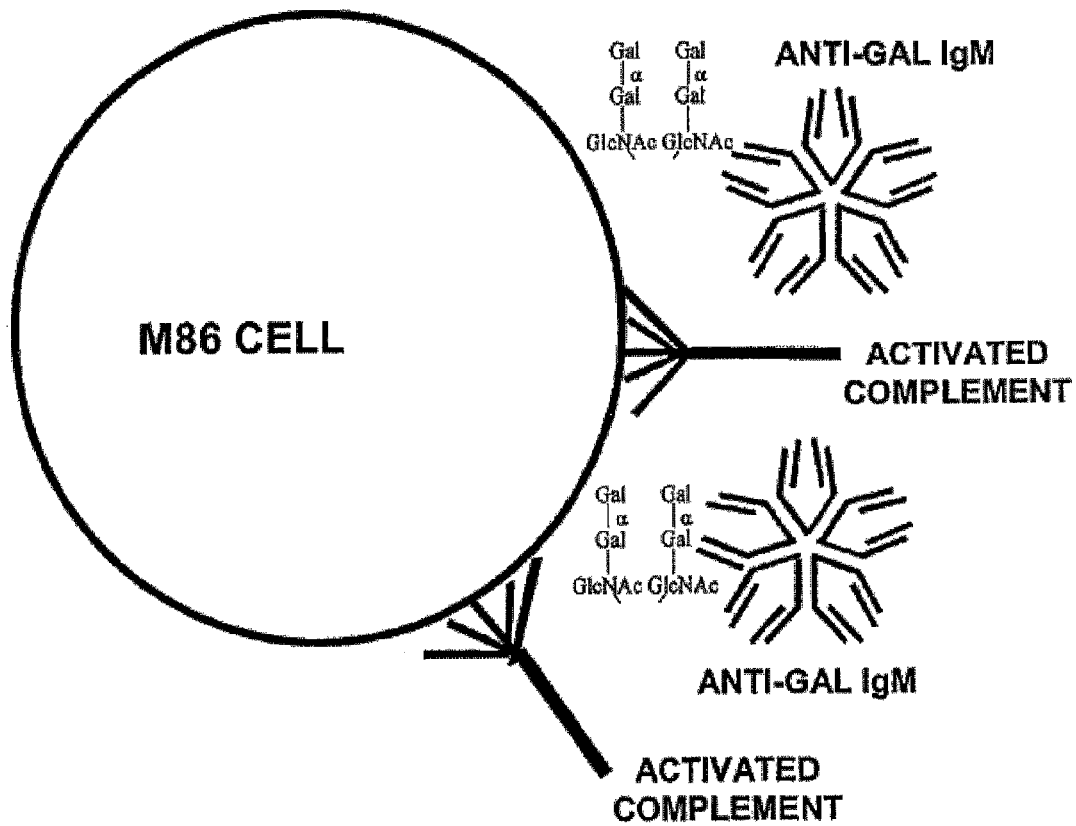
FIG. 4A shows a schematic for complement activity involving the lysis of the anti-Gal producing hybridoma cells M86.
Figure 4B:
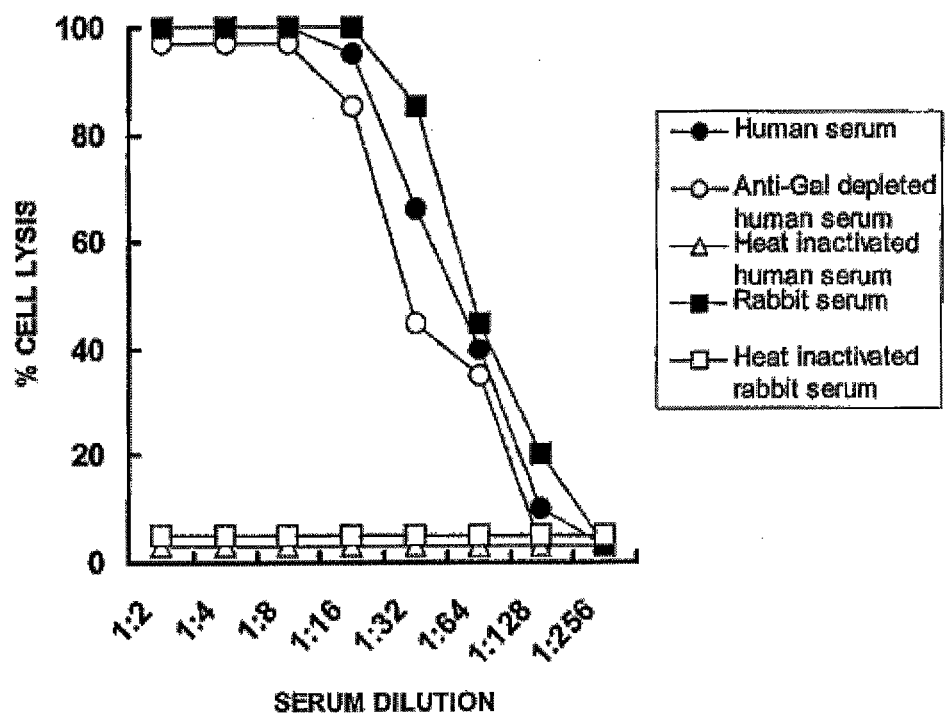
FIG. 4B provides a graph of showing the lysis of M86 cells by complement after incubation at 37° C. for 1 h.

This example describes the activation of complement within serum as a result of the binding of serum anti-Gal antibodies to α-gal epitopes on α-gal liposomes. Complement activation was observed herein by measuring the consumption of complement (e.g., loss of complement ability to lyse cells with bound antibodies). The binding of anti-Gal to α-gal epitopes on α-gal liposomes results in complement consumption due to conversion of the activated complement into complement fragments. The hybridoma cell line M86, which secretes an anti-Gal mAb, was used as a readout system for measuring complement mediated cytolysis (e.g., presence of complement in the serum). Since M86 cells express α-gal epitopes, the anti-Gal IgM mAb they produce bind to the α-gal epitopes on the hybridoma cell surface as schematically illustrated in FIG. 4A. When complement is added, it is activated by the anti-Gal bound to α-gal epitopes on the M86 cells, ultimately resulting in complement mediated lysis of the M86 cells as provided for in Galili et al., *Transplantation* 65, 1129 (1998), hereby incorporated by reference. Incubation of M86 cells with human serum at various dilutions, for 1 h at 37° C. (●) results in more than 40% lysis of the M86 cells even at a serum dilution of 1:64 (FIG. 4B). Lysis of M86 cells does not require exogenous anti-Gal since these cells have autologous anti-Gal bound to the α-gal epitopes of the cell surface. Thus, human serum depleted of anti-Gal also induces M86 lysis, due to the complement activity present in human serum (○). Anti-Gal depletion can be achieved by incubation of the human serum with glutaraldehyde fixed RBC, which express an abundance of α-gal epitopes. The adsorption of anti-Gal on fixed rabbit RBC was performed on ice to prevent complement activation during the adsorption process. Rabbit serum (which lacks anti-Gal like serum from all other nonprimate mammals) has complement and thus can lyse more than 40% M86 cells even at a dilution of 1:64. Incubation at 56° C. for 30 min of both human serum (Δ) and rabbit serum (□) results in inactivation of complement and hence loss of lytic activity (FIG. 4B).

Figure 4C:
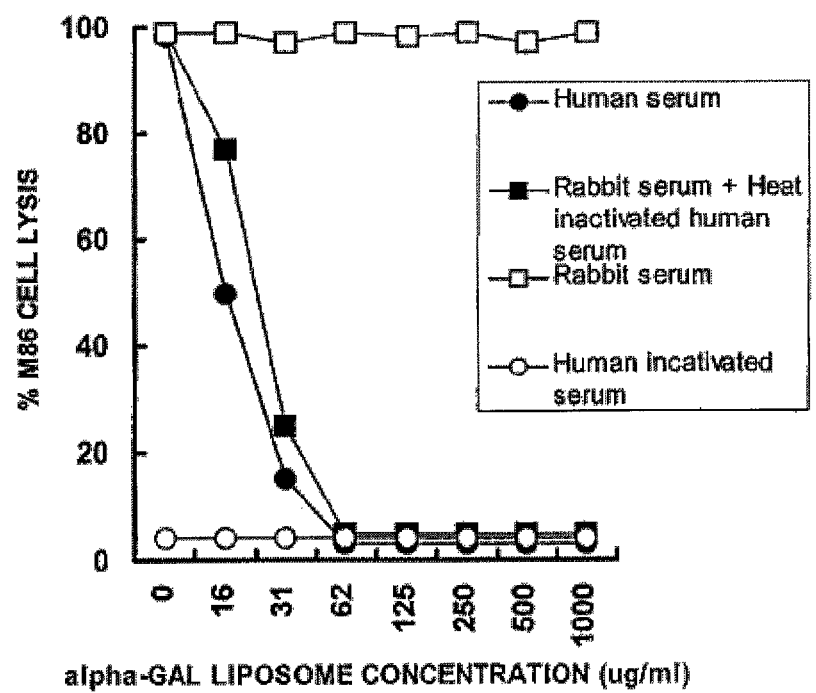
FIG. 4C provides a graph showing that interaction of human serum anti-Gal with α-gal liposomes results in complement consumption as measured by a loss of serum lytic activity. Human serum at a dilution of 1:10 was co-incubated with α-gal liposomes at various concentrations of the liposomes for 2 h at 37° C.

Addition of α-gal liposomes to the human serum diluted 1:10 for 30 min at 37° C., prior to addition of M86 cells, resulted in the loss of complement mediated cytolysis of the M86 cells even at a concentration of 62 µg/ml of the α-gal liposomes (FIG. 4C). Loss of lytic activity is presumed to occur as a result of the consumption of serum complement due to anti-Gal binding to α-gal liposomes. Thus, subsequent addition of M86 cells and incubation of the mixture for 1 h at 37° C. results in no significant M86 cell cytolysis, whereas in the absence of α-gal liposomes the complement in human serum lyses 100% of the M86 cells. Similarly, the complement in normal rabbit serum diluted 1:10 lyses more than 95% of M86 cells. However if the rabbit serum is incubated with α-gal liposomes and with heat inactivated human serum, no significant M86 lysis is observed when these cells are added to suspensions containing 62 µg/ml of α-gal liposomes. This lack of cell lysis is the result of the rabbit complement consumption due to the human anti-Gal binding to the α-gal liposomes and inactivation of the rabbit complement, prior to the addition of M86 cells. These data indicate that binding of anti-Gal to α-gal liposomes in vivo will also result in complement activation and therefore to the generation of C5a and C3a chemotactic factors, which is always part of the complement activation process.

Example 3

Induction of Monocyte and Macrophage Migration

Figure 5:
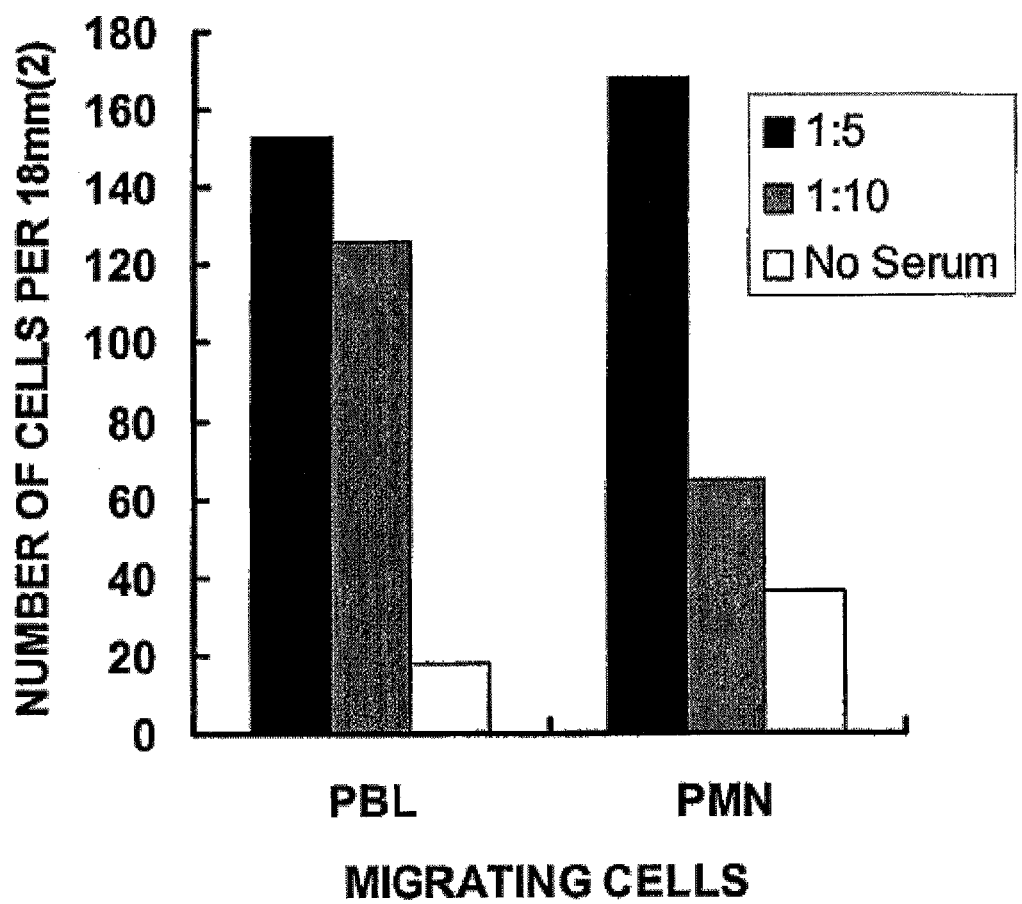
FIG. 5 shows the migration of human monocytes and neutrophils, or of mouse macrophages in response to chemotactic gradients generated by complement activation following anti-Gal binding to α-gal liposomes. The analysis was performed in a Boyden chamber system. This system includes two chambers, with the lower chamber containing human serum mixed with α-gal liposomes and the upper chamber containing various peripheral blood mononuclear cells (PBMC) or polymorphonuclear cells (PMN). The two chambers are separated by a porous filter (e.g., 8 μm pores), which permits the migration of cells between the chambers. The size of the migration area is 18 mm$^2$. After 24 h at 37° C. the filters were washed and stained, and the number of cells migrating toward the lower chamber were counted. The study was performed with 1×10$^6$ cells/ml in the upper chamber and serum diluted 1:5 and 1:10, mixed with 1 mg/ml of α-gal liposomes, in the lower chamber. Open columns indicate the number of migrating cells in the absence of serum; closed columns indicate the number of migrating cells with serum dilution 1:5; and gray columns indicate the number of migrating cells with serum dilution 1:10.

This example describes the chemotactic gradient generated by complement activation as a result of serum anti-Gal binding to α-gal liposomes. The generation of complement C5a and C3a chemotactic factors was assessed by monitoring the migration of monocytes and macrophages in a Boyden chamber. This system includes two chambers, a lower chamber containing serum mixed with α-gal liposomes and an upper chamber containing various white blood cells. The two chambers are separated by a porous filter that permits the migration of cells from the upper to the lower chamber via pores within the filter. At the end of a 24 h incubation period at 37° C. the filters are stained and the number of migrating cells (e.g., within lower chamber) is counted. The study was performed with $10^6$ cells/ml in the upper chamber and serum diluted 1:5 (black columns) or 1:10 (gray columns) and mixed with 1 mg/ml of α-gal liposomes in the lower chamber. A negative control solution in the lower chamber contained medium and α-gal liposomes, in the absence of serum, in order to assess the random migration of cells (open columns). As shown in FIG. 5, incubation of human peripheral blood lymphocytes (PBL) or polymorphonuclear cells (PMN) in the upper chamber and α-gal liposomes in the absence of serum in the lower chamber did not induce significant cell migration. However when serum and α-gal liposomes were mixed together in the lower chamber, extensive migration of mononuclear cells and neutrophils was observed toward the lower chamber. The morphology of the migrating cells in the PBL population indicated that the majority of the migrating cells were monocytes.

Example 4

Intradermal Recruitment of Neutrophils, Monocytes and Macrophages

In vivo studies on the effect of α-gal liposomes were performed in α-1,3galactosyltransferase knockout (KO) mice as provided for in Thall et al., *J. Biol. Chem.* 270, 21437-21442 (1995), incorporated in its entirety by reference, since these are the only non-primate mammals capable of producing anti-Gal antibodies. All other non-primate mammals express α-gal epitopes and thus do not produce anti-Gal antibodies. In order to monitor the in vivo effect of anti-Gal interaction with injected α-gal liposomes, KO mice producing anti-Gal (e.g., KO mice pre-immunized with 50 mg pig kidney membranes resulting in the induction of anti-Gal titers similar to those observed in humans) were injected intradermally with 1.0 mg α-gal liposomes in 0.1 ml saline.

Figure 6:
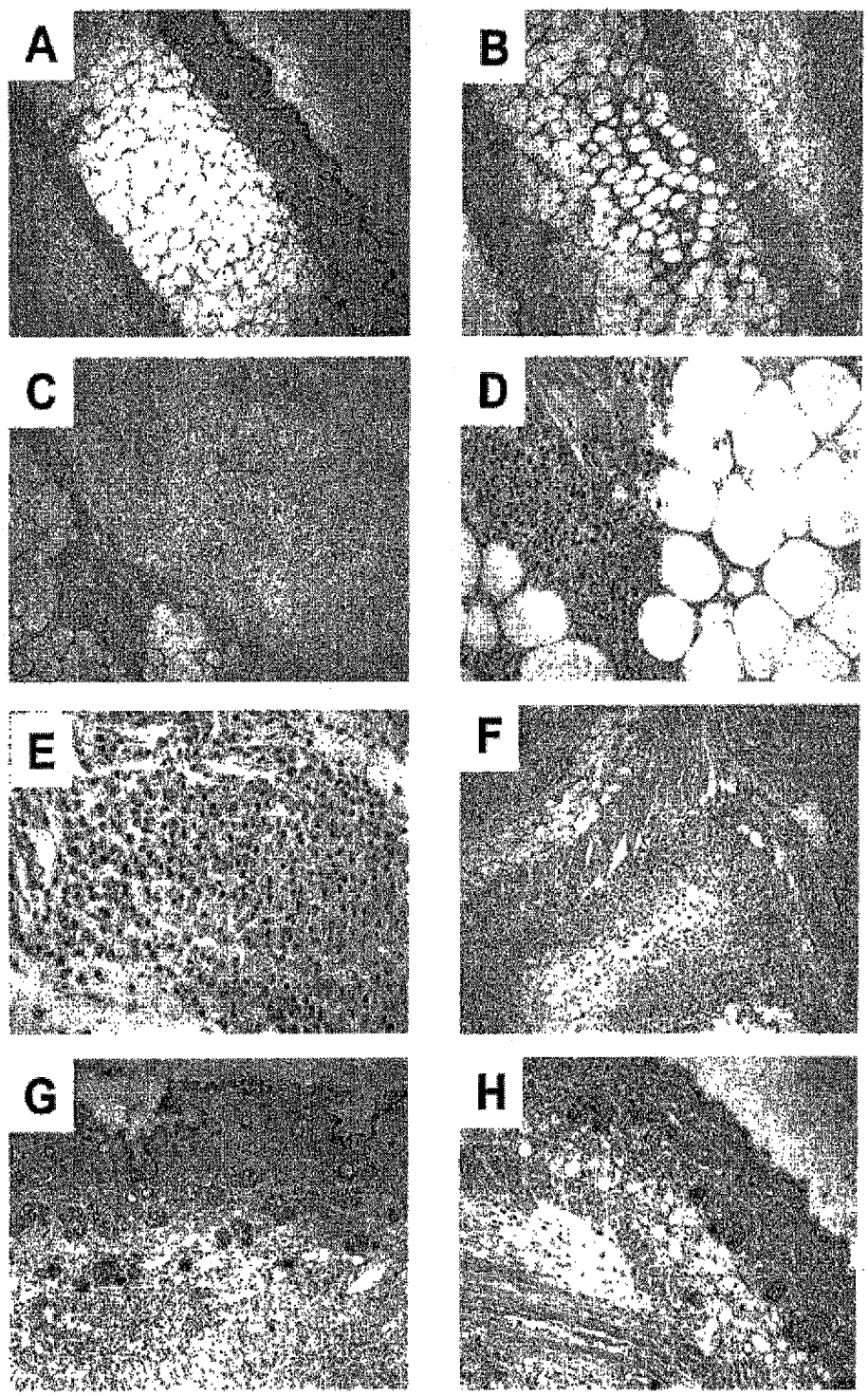
FIG. 6 depicts the in vivo induction of local inflammation by intradermal injection of α-gal liposomes in KO mice. The KO mice were immunized three times intraperitoneally with a homogenate of 50 mg pig kidney membranes to induce anti-Gal production. The KO mice were injected intradermally with 1 mg α-gal liposomes suspended in 0.1 ml saline, and euthanized at different time points post-injection. Skin specimens at the injection site were removed, sectioned, stained with hematoxylin-eosin (H&E) and inspected microscopically. Some of the sections include the epidermis layer as point of reference.

Skin specimens from the injection site were obtained at different time points, fixed, stained with hematoxyllin-eosin (H&E) and inspected under a light microscope. FIG. 6A depicts normal skin prior to injection of α-gal liposomes. The epidermis comprises of one to two layers of epithelial cells. The dermis contains fibroblasts under the epidermal layer, fat cells as a deeper layer and an underlying narrow layer of muscle cells and fibroblasts. No inflammatory cells are observed in the normal skin (×100). FIG. 6B depicts the skin 12 h after injection of 1.0 mg α-gal liposomes. The intradermal injection site is identified as the area with the least amount of cells, under the muscle cell layer. Note that at this early time point the injection area is filled with neutrophils that surround the injected site both within the fat cell layer and within the side adjacent to the epidermis (×100). FIG. 6C also depicts the skin 12 h post-injection. The α-gal liposome depot of the injection site is shown in the center of image, which is bordered on the left by the fat cell layer. The α-gal liposome injection site has a low density of dermal cells. However, by 12 h post-injection, the injection site has become populated by infiltrating inflammatory cells presumably recruited by the injected α-gal liposomes bind to anti-Gal antibody and complement activation. A higher magnification of the infiltrating cells within the fat cell area in FIG. 6D (×400) indicates that the infiltrating cells are neutrophils. The extensive migration of neutrophils into the α-gal liposome injection site is followed by migration of monocytes and macrophages, which are recruited by the locally produced complement chemotactic factors. FIG. 6E depicts the α-gal liposome injection site 48 h post-injection. As shown in this higher magnification (×400) most of the infiltrating inflammatory cells in the injection site are mononuclear cells with nuclear features resembling macrophages (e.g., kidney shaped nuclei). These cells are evident in the injection site already 24 h post-injection. The characterization of these cells as macrophages is further described in Example 6 below. FIG. 6F depicts the α-gal liposome injection site 5 days post-injection. By this time the injection site is filled with large round macrophages, reflecting the local activation of the infiltrating macrophages due to the interaction of the anti-Gal opsonized α-gal liposomes. Only the center of the injection site is devoid of macrophages, and likely functions as an α-gal liposome depot. The epidermis in this figure is shown in the upper left corner. As shown in FIG. 6G, infiltrating macrophages are detectable in the injection site as late as 14 days post-injection. As shown in FIG. 6H, macrophages completely disappear from the injection site by day 20 post-injection. The injection site at that stage is rich with fibroblasts and muscle cells, which are contemplated to have originated from myofibroblasts recruited by the macrophages activated by the anti-Gal opsonized α-gal liposomes. Nonetheless an understanding of the mechanism is not necessary in order to make and use the present invention. The histological analysis presented in FIG. 6 indicates that intradermal injection of α-gal liposomes is suitable for induction of a local inflammatory response. The localized inflammatory response is detectable within 12 h and is accompanied by extensive neutrophils infiltration, followed by a second wave of infiltrating monocytes and macrophages within 24-48 h post-injection. In skin wounds accompanied by microbial infection, the neutrophils and the macrophages recruited by the interaction between anti-Gal and the injected α-gal liposomes are contemplated to mediate the destruction of the infectious agent. In addition, the various growth factors, cytokines and chemokines secreted by the activated macrophages are contemplated to mediate wound healing and repair of the damaged tissue. Nonetheless an understanding of the mechanism(s) is not necessary in order to make and use the present invention.

Example 5

α-Gal Liposomes do not Elicit an Immune Response

Figure 7:
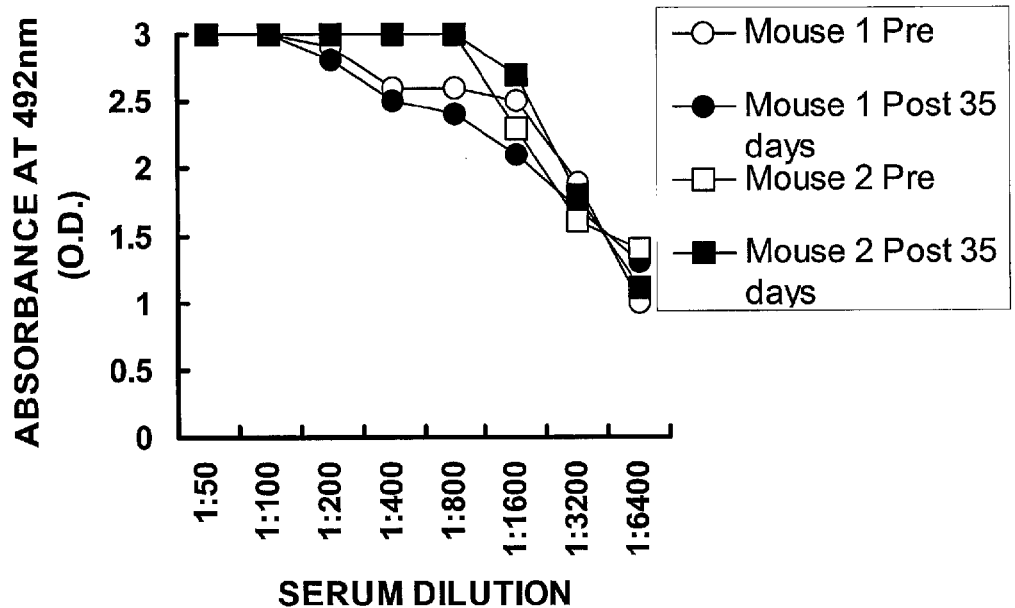
FIG. 7 provides a graph depicting the lack of antibody response to injected α-gal liposomes. The antibody response was measured in an ELISA with 50 μl of α-gal liposomes at concentration of 100 μg/ml dried in each well (solid phase antigen). The dried α-gal liposomes were subsequently blocked with 1% BSA in PBS. Serum samples from two representative mice obtained before and 35 days post intradermal injection (○,● and □,■), were tested for IgG binding to α-gal liposomes. No significant differences are observed in anti-α-gal liposomes IgG antibody activity in serum from mice obtained post α-gal liposome injection (closed symbols).

Although α-gal liposomes readily bind in vitro and in vivo to anti-Gal antibodies, they do not elicit an immune response against the injected α-gal liposomes as determined by ELISA. To demonstrate this, 50 μl of a solution containing α-gal liposomes at a concentration of 100 μg/ml were dried in ELISA wells to serve as a solid phase antigen. Serum samples from two representative mice obtained before (○ and □) and 35 days post intradermal injection (● and ■, respectively) were tested for IgG binding to α-gal liposomes. A humoral immune response against components of the α-gal liposomes should result in increased IgG binding to α-gal liposome-coated wells in post-injection serum (e.g., higher activity as compared to pre-injection serum). As shown in FIG. 7, the binding of IgG antibodies to α-gal liposomes 35 days post-injection was similar or lower to that observed prior to injection. Thus administration of α-gal liposomes does not elicit a deleterious humoral immune response against the injected material, despite their ability to recruit neutrophils, monocytes and macrophages to the injection site.

Example 6

Figure 8:
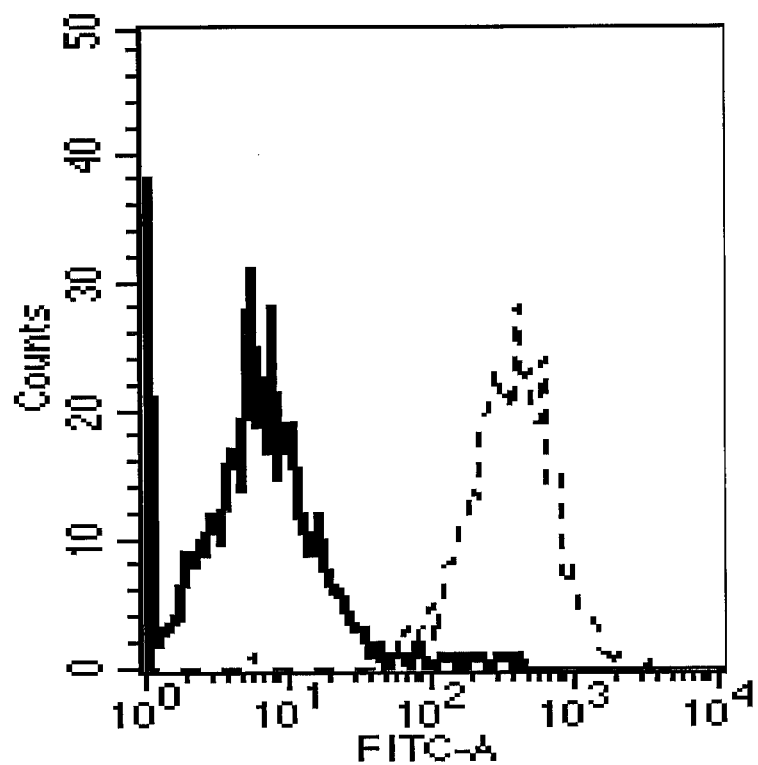
FIG. 8 provides exemplary data demonstrating in vivo recruitment of macrophages into polyvinyl alcohol (PVA) sponge containing α-gal liposomes. The sponge filled by soaking with α-gal liposome suspension (100 mg/ml) was implanted subcutaneously in α-1,3-galactosyltransferase knockout mice (KO mice) for 3 days, then removed. The infiltrating cells were obtained by repeated squeezing of the sponge in 1 ml PBS. The cells were stained with anti-CD11b antibody (Pharmingen, Inc,) that specifically binds to macrophages and allows for the identification of macrophages by flow cytometry (FACS) analysis. Solid line—isotype control of cells stained only with the secondary FITC coupled anti-rat IgG antibody. Broken line—cells stained with monoclonal rat anti-mouse CD11b Ab, then with secondary fluorescein coupled anti-rat IgG antibody. Note the shift of the whole cell population to the right, implying that all cells migrating into the PVA sponge containing α-gal liposomes, are macrophages. A representative mouse is shown.

Recruitment of Macrophages into Polyvinyl Alcohol (PVA) Sponges by α-Gal Liposomes The objective in this study was to determine whether the mononuclear cells recruited by injected α-gal liposomes binding the anti-Gal antibody (FIG. 6) are macrophages that can be identified by immunostaining and analysis of stained cells by flow cytometry. This was performed by the use of subcutaneously implanted polyvinyl alcohol (PVA) sponge discs (PVA Unlimited, Inc., 10 mm diameter and 3 mm thickness). Prior to implantation, the discs were soaked in a suspension of α-gal liposomes (100 mg/ml). α1,3galactosyltransferase knockout mice (KO mice) were anaesthetized with 0.04 cc of ketamine/xylazine (50 mg/cc and 2.5 mg/cc, respectively). The dorsa of the mice are shaved and a 10 mm linear incision was made then implanted subcutaneously with the PVA disc soaked in α-gal liposome suspension. The wound was closed by suture. The PVA discs were removed from the mice 72 h post implantation. The present invention teaches that anti-Gal binds to the α-gal liposomes, activates complement and recruit inflammatory cells into the PVA sponge discs. The cells migrating in vivo into the PVA sponge discs were retrieved by repeated pressing on sponge discs immersed in PBS. Subsequently, the cells were washed, stained with the mouse monoclonal anti-CD11b macrophage specific antibody (Pharmingen Inc, CA) and subjected to flow cytometry (FACS). As shown in FIG. 8, all infiltrating cells were found to be macrophages, since all cells displayed shift to the right after staining with anti-CD11b antibody (broken line) in comparison to isotype control (solid line). Thus, all infiltrating cells were stained positively with the macrophage specific monoclonal antibody. PVA discs soaked with saline and studied 3 days post implantation contained no measurable numbers of infiltrating cells.

Example 7

Effects of α-Gal Ointment Application on Wound healing

The α-gal ointment is another composition containing α-glycolipids that can be used for accelerated wound healing by recruitment of macrophages to the damaged area. It is of particular beneficial use in skin burns. The α-gal ointment is prepared by mixing α-gal glycolipids with Vaseline or any other cream or gel at a final concentration ranging from 0.001% to more than 90% α-gal glycolipids. The α-gal glycolipids may or may not be purified from the mixture with phospholipids and cholesterol obtained by extraction from rabbit red blood cell membranes (described in Example 1). The α-gal ointment is applied topically onto such as, but not limited to skin burns. Burns may be caused by various injuries (e.g., hot objects, hot fluids or radiation). The illustration in FIG. 9 describes treatment of a burn with α-gal ointment. This treatment is applicable to other types of wounds as well. The natural anti-Gal antibody and complement proteins are among the serum proteins that leak from the damaged blood vessels into the burn area because of their high concentration in the serum. As illustrated in FIG. 9, the interaction of the natural anti-Gal antibody in the burn with the large amounts of α-gal glycolipids in the ointment induces local activation of the complement cascade, and thus, generates the complement fragments chemotactic fragments C5a and C3a that recruits macrophages to the area of this antibody binding to its antigen. This extensive recruitment of macrophages, which is much faster than the physiologic migration of macrophages into burns, results in accelerated debridement, epithelialization, fibroblasts migration and proliferation and collagen matrix deposition by the fibroblasts (fibroplasia), ultimately resulting in accelerated healing of burns and shorter morbidity than that achieved with current treatments. This treatment is applicable to various skin injuries where anti-Gal will leak from damaged capillaries and thus will interact with α-gal glycolipids within the applied α-gal ointment. α-Gal ointment may also be formed with ointments containing antibiotics (as those presently used for burns treatment), thus preventing infections while the healing process occurs. This treatment of topical application of α-gal glycolipids in an ointment formulation introduces no chemicals, other than the natural α-gal epitopes on glycolipids. Phospholipids and cholesterol, if present, are identical to those in human cells. Therefore, this treatment is likely to be safe. The safety of α-gal glycolipids is further implied from the fact that humans are constantly exposed to α-gal epitopes via a wide range of foods containing beef and pork meat, without any adverse effects.

Example 8

Binding of Anti-Gal to α-Gal Glycolipids in α-Gal Ointment

Figure 10:
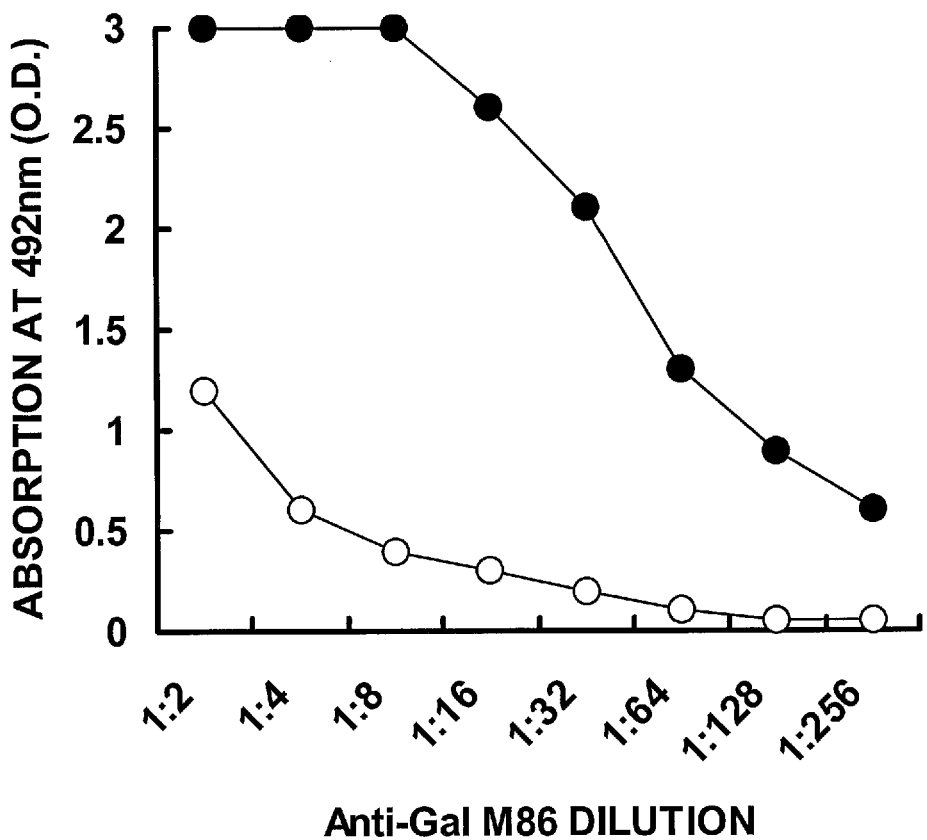
FIG. 10 demonstrates one embodiment of an interaction between an anti-Gal antibody and α-gal glycolipids within α-gal ointment. Neutralization of monoclonal anti-Gal following mixing with α-gal ointment (○), or Vaseline control lacking α-gal glycolipids (●). Anti-Gal activity was determined by subsequent binding to α-gal epitopes linked to BSA (α-gal BSA) as solid phase antigen in ELISA wells.

The interaction between the anti-Gal antibody and α-gal epitopes in α-gal ointment is demonstrated. The α-gal ointment can not be used as solid phase antigen in ELISA since it does not attach to ELISA wells. Thus, the accessibility of α-gal epitopes within the ointment to anti-Gal binding was tested by mixing of the monoclonal anti-Gal M86 antibody as provide for in Galili et al., *Transplantation* 65, 1129, 1998, hereby incorporated by reference, with the ointment at a 1:1 ratio (vol/vol) for 1 h at 37° C. Interaction of anti-Gal with α-gal epitopes in the ointment prevents (neutralizes) subsequent binding of the monoclonal anti-Gal antibody to α-gal epitopes on the synthetic α-gal epitopes linked to bovine serum albumin (α-gal BSA), which serves as solid phase antigen in ELISA. This provides a readout system for non-neutralized anti-Gal remaining active. Mixing the antibody preparations with Vaseline served as control for lack of α-gal epitopes, i.e. no binding of anti-Gal. α-Gal ointment neutralized >95% of the monoclonal anti-Gal M86 antibody mixed with the ointment as shown in FIG. 10. In the absence of α-gal glycolipids, Vaseline had no neutralizing effect on anti-Gal. This implies that anti-Gal in burn areas will readily bind to α-gal epitopes in α-gal ointment that is applied topically.

Example 9

Effect of α-gal Ointment on Burn Healing Following Thermal Injury

Figure 11:
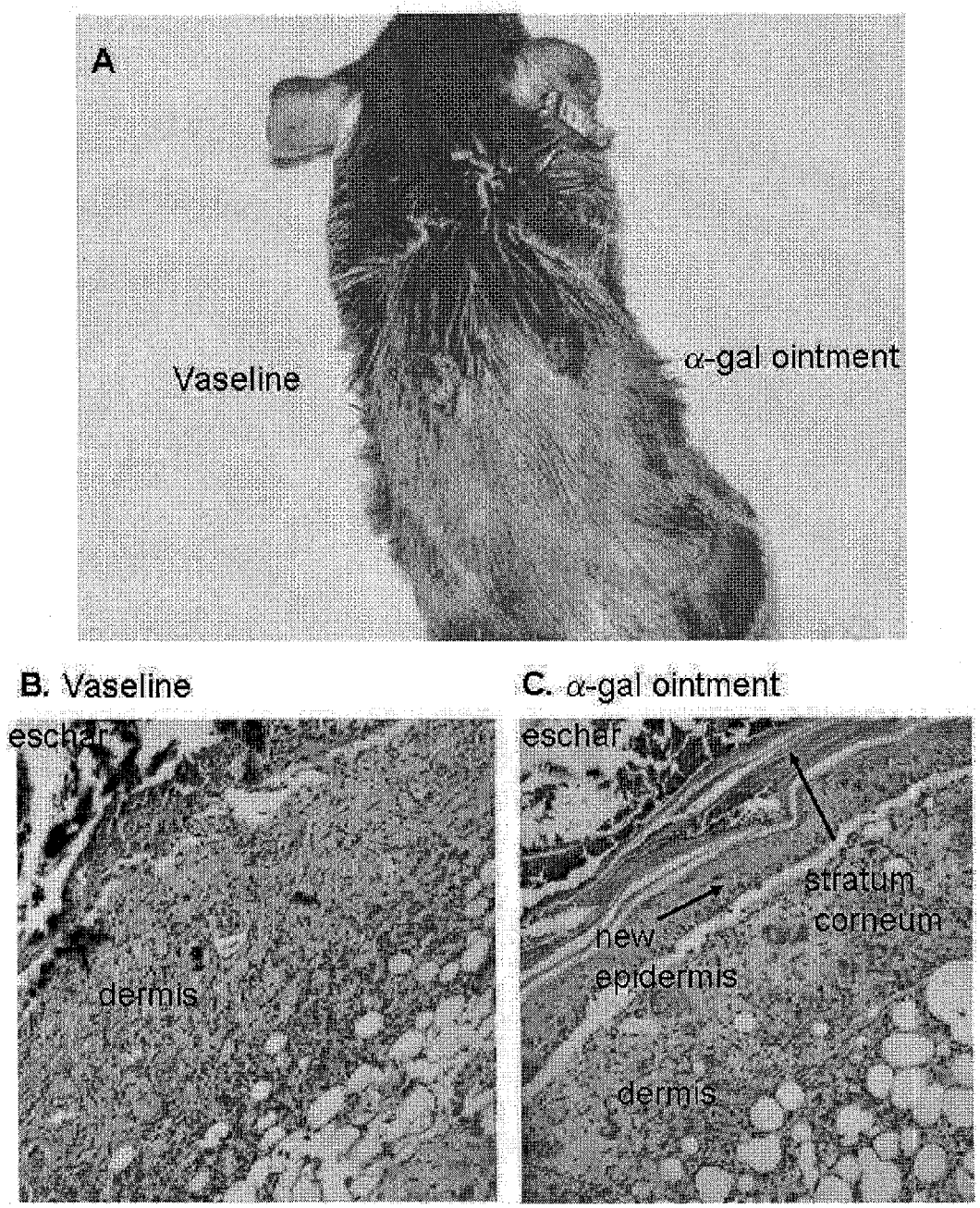
FIG. 11 provides exemplary data showing the effects of α-gal ointment on healing of burns induced by thermal injury to the skin. α1,3galactosyltransferase KO mice confirmed to produce anti-Gal in titers comparable to those in humans, were anesthetized and two burns were made on their backs by thermal injury with the heated bend end of a small metal spatula. One burn (left) was covered with Vaseline and the other (right) with α-gal ointment comprised of α-gal glycolipids mixed with Vaseline. Subsequently, burns were covered with small round band-aids. After six days the band-aids were removed from the burns. As shown in (A), the burn treated with α-gal ointment healed significantly faster than that with Vaseline and its size was ~50% of the Vaseline treated burn. Histological analysis of these burns demonstrated in the Vaseline treated burn (B) that the dermis was not covered by epidermis to replace the tissue damaged by the burn. The dark fragments on the skin are the damaged epidermis in the form of debris (crust) covering the wound and referred to as "eschar". The α-gal ointment treated wound (C) also has eschar caused by the burn. However, the skin is covered by a new multilayered epidermis comprised of epithelial cells covered by the keratinous layer (stratum corneum, stained-pink). Data are of one of 4 mice with similar results.

This section demonstrates the effects of α-gal ointment on healing of burns in α1,3galactosyltransferase knockout mice (KO mice) producing the anti-Gal antibody. KO mice were deeply anaesthetized with ketamine/xylazine injection and a superficial skin burn was caused in two sites on the back by brief touch with a heated end of a small metal spatula bend in the end (5 min from the tip). Subsequently, α-gal ointment (FIG. 9) was applied topically to the right burn, whereas the left burn was covered with Vaseline lacking α-gal glycolipids. The left burn served as a control for healing of the burn in the absence of anti-Gal interaction with α-gal epitopes. The wounds were covered with circular band-aids. The mice (n=4) were euthanized on Day Six, the skin areas in the burn regions inspected and removed. The skin specimens were fixed with formalin and subjected to histological sections and hematoxyllin-eosin (H&E) staining (FIG. 11).

The burns were of the same size when formed by the heated edge of the metal spatula. However, after six days post-burn, the size of the damaged area treated by topical application of α-gal ointment, was approximately half the size of the control wound treated with Vaseline (FIG. 11A). Histological analysis of the control Vaseline covered burns revealed the absence of the epithelial cells of the epidermis (FIG. 11B). The presence of the debris comprised of dead tissue and granulocytes (eschar) is evident as dark fragments above the injured skin. A similar eschar is observed over the burn covered with α-gal ointment (FIG. 11C). However, the skin treated with α-gal ointment was completely covered at the burn area by a new epidermis consisting of several layers of epithelial cells, as well as a keratinous layer over this epithelial layer (stratum corneum) (FIG. 11C). These findings indicate that within a period of six days, the topical application of α-gal ointment results in complete regeneration of the top layer of the skin and the formation of an epidermis barrier that seals off the dermis from any microbial agent. It should be noted that at this early stage of burn healing, no skin appendages (e.g. hair shafts or sweat glands) are observed as yet. Overall, these findings imply that the histological analysis fits the gross morphology findings of accelerated healing of burns treated with α-gal ointment.

Example 10

Effects of α-Gal Liposome/Anti-Gal Antibody Application on Regeneration and Repair of Damaged Cartilage in Subjects with Osteoarthritis This example is aimed to study the efficacy of the compositions and methods of the present invention in recruitment of mesenchymal stem cells, or stem cells from any origin, for the healing and repair of damaged or injured tissues. In this example α-gal liposomes are injected into either the synovial cavity or the cartilage of human subjects having damaged articular cartilage in the joints, including but in no way limited to the knee joints of subjects with osteoarthritis. The α-gal liposomes are injected at any volume that is suitable for injection into the synovial cavity, with a preferred concentration ranging from 0.01 and 500 mg/ml. The injection is given once or several times in interval of one to several weeks. The anti-Gal antibody interaction with α-gal epitopes on α-gal liposomes results in activation of complement and local production of the complement fragments C5a and C3a, which are potent chemotactics. These factors induce recruitment of neutrophils, monocytes and macrophages into the synovial cavity or into cartilage, ultimately resulting in tissue repair. The Fcγ receptors on macrophages bind the Fc portion of anti-Gal coating the α-gal liposomes due to anti-Gal binding to α-gal epitopes on these liposomes. This Fc/Fcγ receptor interaction generates a signal that activates the macrophages recruited by the C5a and C3a chemotactic factors. Activated macrophages mediate debridement of the damaged cartilage and through secretion of growth factors and cytokines direct migration of stem cells that differentiate locally into chondroblasts in the damaged cartilage. The chondroblasts in turn secrete collagen and other cartilage matrix proteins and polysaccharides, resulting in repair and remodeling of the damaged articular cartilage within the treated joint. Similarly, macrophages activated by the binding of α-gal liposome/anti-Gal antibody complexes mediate debridement of the damaged bone and through secretion of growth factors and cytokines recruit osteoclasts and osteoblasts into the injection site for repair and remodeling of the damaged bone. By analogy, similar injection of α-gal liposomes into damaged heart tissue (myocardium) will result in local recruitment of monocytes/macrophages into the injection site and the subsequent secretion of growth factors and cytokines by these cells recruited into the injection sites. These growth factors and cytokines direct the migration of stem cells, either from the adjacent tissue or from another source, into the damaged tissue and further direct the subsequent repair and remodeling of the damaged heart tissue. Similarly, injection of α-gal liposomes into other damaged or inured tissues in the body may result in accelerated repair of the injury by recruitment of stem cells by a mechanism similar to that described above for the damaged articular cartilage treated with α-gal liposomes.

Example 11

Figure 12:
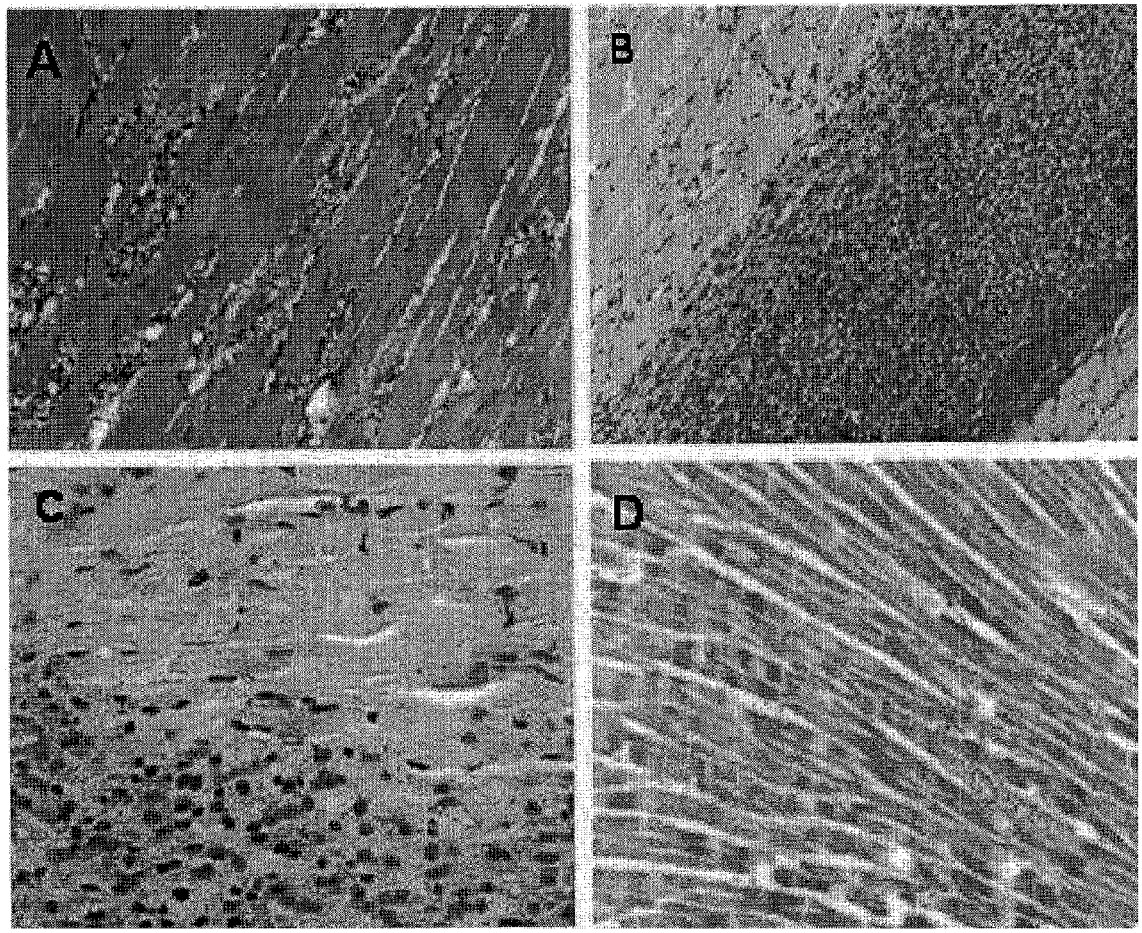
FIG. 12 provides exemplary data showing rapid recruitment of macrophages into ischemic heart muscle injected with α-gal liposomes in mouse heart implanted subcutaneously (Hematoxyllin & Eosin staining). Hearts removed from KO mice were injected into the myocardium with 2 mg α-gal liposomes, or with saline. Subsequently, the hearts were implanted subcutaneously in KO mice producing anti-Gal.

In Vivo Recruitment of Macrophages by α-Gal Liposomes Injected into Ischemic Heart Muscle This example demonstrates the ability of α-gal liposomes to recruit macrophages into the heart muscle. Hearts removed from KO mice were injected into the myocardium with 2 mg α-gal liposomes or with saline. Subsequently, the hearts were implanted subcutaneously in KO mice producing anti-Gal. Implanted hearts injected with saline and removed after 2 weeks contained necrotic cardiomyocytes and infiltrating neutrophils (FIG. 12A). After 4 weeks the heart implants disappeared due to the destruction of the organ. In contrast, myocardium specimens from implanted hearts that were injected with α-gal liposomes tissue maintained normal histological structure for 2 and 4 weeks and contained many recruited macrophages (FIGS. 12B and 12C). In addition, many of the recruited cells migrate into areas between the dead cardiomyocytes (FIG. 12C). All the nuclei visible in the sections are those of the infiltrating cells. This is indicated in FIG. 12D which describes an inner portion of the myocardium which lacks infiltrating cells. As seen in FIG. 12D (2 weeks post implantation of an α-gal liposomes injected KO mouse heart,) no nuclei are visible in the dead cardiomyocytes. Moreover, the myocardium in α-gal liposomes treated mice maintains its histological characteristics much better than saline injected hearts (FIGS. 12B-D, vs. FIG. 12A).

Example 12

Figure 13:
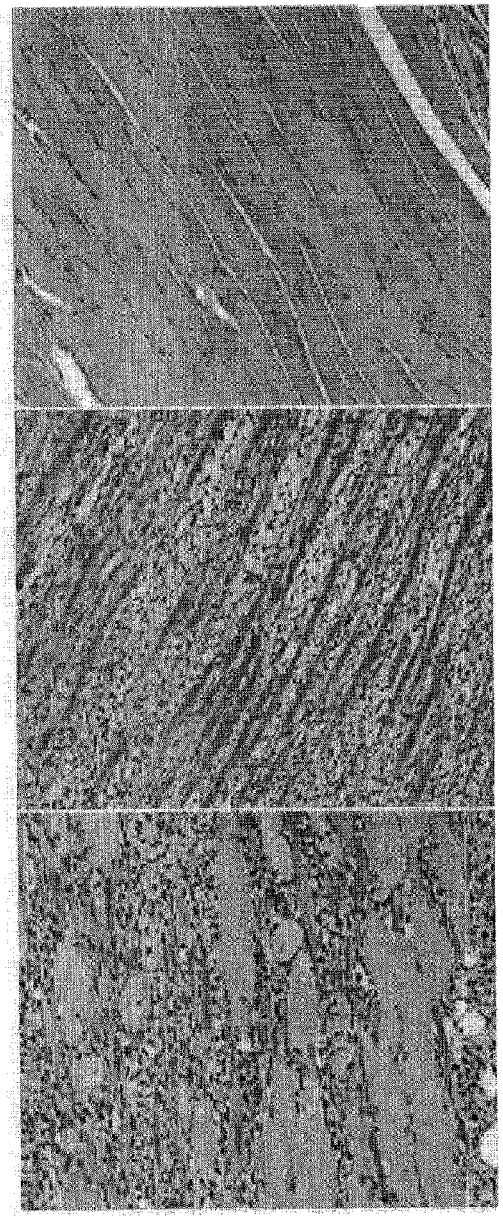
FIG. 13 presents exemplary data showing rapid infiltration of macrophages into ischemic leg muscle treated with α-gal liposomes by intramuscular injection of 10 mg α-gal liposomes. The study was performed in anti-Gal producing KO mice in which the blood flow is blocked in the right hind leg by applying a rubber band tourniquet over the leg. The tourniquet is removed after 4 h to allow for reperfusion of the leg blood vessels. The histology studies are performed in the leg muscle *Tibialis anterior.*

In Vivo Recruitment of Macrophages by α-Gal Liposomes into Ischemic Skeletal Muscle Another example for the in vivo recruitment of macrophages by α-gal liposomes is the injection of these liposomes into a KO mouse leg muscle by ischemia. The blood flow was blocked in the right hind leg of KO mice by applying a rubber band tourniquet over the leg according to a method previously described by Ott et al., *FASEB J.* 19:106 (2005). The tourniquet was removed after 4 h to allow for reperfusion of the leg blood vessels. The histology studies are performed in the leg muscle (hind limb). The muscle fibers in an uninjured skeletal muscle comprise of muscle cell syncitia (myotubes), formed by fusion of myoblasts, with the nuclei in the periphery of the tubes. See, FIG. 13A. This ischemia results in death of the myotubes due to lack of oxygen. The resulting necrosis of the myotubes is clearly evident after 96 h. See, FIG. 13B. The specimen in FIG. 13B was injected with saline to serve as control to α-gal liposomes injection. At that time, many neutrophils infiltrate the necrotic tissue. The myotube syncitia decrease in their size and the nuclei of each myotube accumulate in a row. Subsequently, the dead myotubes are phagocytozed by debriding macrophages. Other ischemic leg muscles were injected with 10 mg α-gal liposomes immediately after removal of the tourniquet that prevented for 4 h blood flow into the muscle. Specimens obtained 4 days post α-gal liposomes injection (FIG. 13C) indicated that the tissue contained many more macrophages than the control tissue injected with saline (FIG. 13B). Moreover, the proportion of non-necrotic myotubes in the α-gal liposomes treated ischemic muscle was much higher than that in saline injected muscle, where the large majority of the myotubes are necrotic (FIGS. 13C vs. 13B respectively). These findings indicate that the injection of α-gal liposomes induces rapid recruitment of macrophages into the skeletal leg muscle and that the rapid migration of the macrophages into the injured tissue reduces the damage caused by ischemia to the muscle.

Example 13

In Vivo Recruitment of Stem Cells by α-Gal Liposomes

Figure 14:
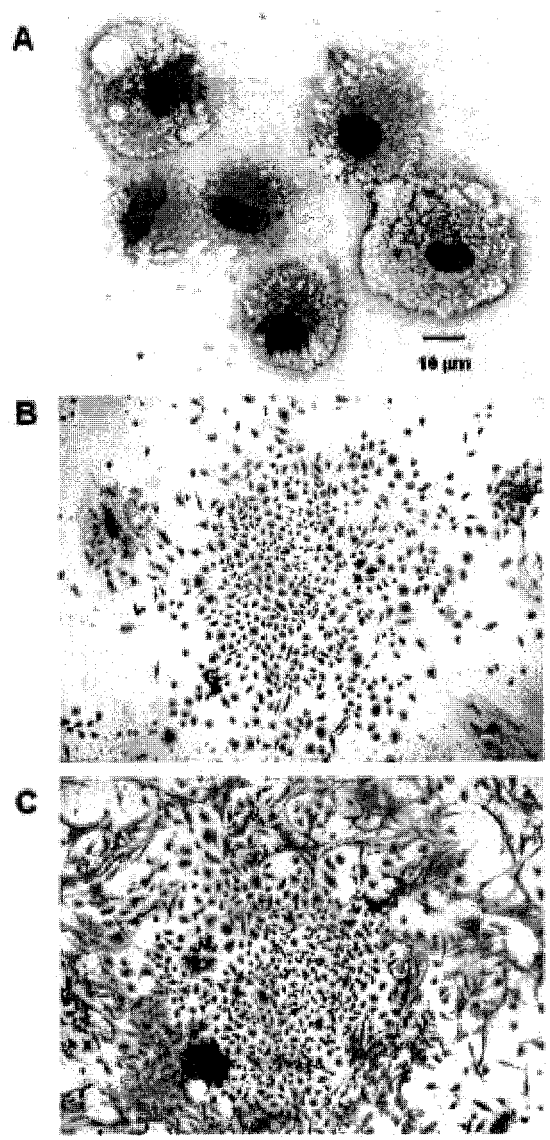
FIG. 14 presents exemplary data showing the presence of cells with stem cell potential among the macrophages recruited into polyvinyl alcohol (PVA) sponge discs by anti-Gal/α-gal liposomes interaction. In view of the ability of stem cells to proliferate in vitro and form cell colonies, the cells migrating into implanted PVA sponge discs, due to chemotactic factors generated by anti-Gal/α-gal liposomes interaction, were tested for the ability to form colonies in vitro. The cells infiltrating into the implanted PVA sponge discs were retrieved and cultured in vitro on round cover slips in tissue culture wells for 5 days. Subsequently, the cover slips were stained with Wright staining.

This example addresses the question of whether the population of macrophages recruited by α-gal liposomes also includes stem cells. Infiltrating macrophages were retrieved from PVA sponge discs containing 10 mg α-gal liposomes that were implanted subcutaneously for 6 days. The macrophages were retrieved by repeated squeezing of the sponge disc in phosphate buffered saline (PBS) and are presented in FIG. 14A. These cells were cultured in vitro on cover slips for 5 days in DMEM medium containing 10% fetal calf serum. Subsequently the cover slips were washed and stained with Wright staining. As shown in FIGS. 14B and 14C, cells which are recruited into PVA sponge discs containing α-gal liposomes, included, in addition to the migrating macrophages, also cells that display an extensive ability to proliferate (200-500 cells per colony formed from one cell within a period of 5 days). The frequency of these colony forming cells among cultured macrophages from PVA sponges to be 3-5 cells/$10^5$ macrophages. This is a similar frequency as that of mesenchimal stem cells in the bone marrow reported by Eisenberg et al., *Stem Cells* 24:1236 (2006). The ability to proliferate (i.e. self renew) and form colonies is one of the main characteristics of stem cells. These findings indicate that the macrophages recruited by anti-Gal/α-gal liposomes interaction, include also cells that have stem cell potential.

Example 14

Regeneration of Injured Brain Tissue by Treatment with α-Gal Liposomes

This example is aimed to study the efficacy of the compositions and methods of the present invention in recruitment of stem cells, for the healing and repair of damaged or injured brain tissue. In this example α-gal liposomes are injected intracranial into areas in the brain of human subjects having damage such as, but not limited to ischemia following infarct in one or more of the blood vessels in the brain. The α-gal liposomes are injected at any volume that is suitable for injection into the injured brain tissue and at a concentration ranging between 0.01 and 500 mg/ml. The interaction between the injected α-gal liposomes and the anti-Gal antibody activates complement and the generated chemotactic complement cleavage peptides recruit monocytes and macrophages to the injection site. The macrophages are activated by Fc/FcγR interaction with anti-Gal coated α-gal liposomes and secrete cytokines and growth factors that promote healing of the injured brain tissue and recruit stem cells. These stem cells proliferate and differentiate in to brain cells that repair and regenerate the injured brain tissue.

Example 15

Regeneration of Injured Peripheral Nerve or Injured Spinal Cord by Treatment with α-Gal Liposomes This example is aimed to study the efficacy of the compositions and methods of the present invention in recruitment of stem cells, for the healing and repair of damaged or injured peripheral nerve or spinal cord. In this example α-gal liposomes at a concentration ranging between 0.01 and 500 mg/ml are injected into the injured spinal cord or in the injured nerve. An alternative approach is that the injured spinal cord or peripheral nerve is surrounded by a device containing α-gal liposomes at a concentration ranging between 0.01 and 500 mg/ml. This device can be in the form of a gel, plasma or fibrin clot surrounding part or the whole injured nerve tissue or spinal cord. Alternatively, collagen sheet or any biodegradable or non-biodegradable sheet containing the α-gal liposomes or having on its surface α-gal liposomes and which can be shaped into a tube around the injured nerve or spinal cord, can be used to apply the α-gal liposomes around the injured nerve or the injured spinal cord. The interaction between the injected α-gal liposomes and the anti-Gal antibody activates complement and the generated chemotactic complement cleavage peptides recruit monocytes and macrophages to the injection site. The macrophages are activated by Fc/FcγR interaction with anti-Gal coated α-gal liposomes and secrete cytokines and growth factors that promote extension of the damaged axons for reconnecting with the distal portion of the damaged neurons. Alternatively, the stem cells recruited by these cytokines and growth factors proliferate and differentiate in to nerve cells that promote regeneration of the injured nerve tissue in the peripheral nerve and/or in the spinal cord. Injection of α-gal liposomes into the retina, lens, or cornea of the eye could be beneficial in the recruitment of stem cells that repair damages in these tissues of the eye.

Example 16

Treatment of Diabetic Patients by Injection of α-Gal Liposomes into the Pancreas This example is aimed to study the efficacy of the compositions and methods of the present invention in recruitment of stem cells, for regenerating the activity of Langerhans Islets in the pancreas of diabetic patients. In patients with Type I diabetes and in some of the patients with Type II diabetes the Langerhans Islets have been destroyed. The proposed treatment aims to restore biologically active Langerhans Islets in the pancreas of these patients, thereby provide endogenous insulin and cure the state of diabetes. In this example, α-gal liposomes at a concentration ranging between 0.01 and 500 mg/ml are injected into the pancreas by endoscopy ultrasound, or by laparoscopy or by any other procedure which enables for direct injection of the α-gal liposomes into the pancreas. The interaction between the injected α-gal liposomes and the anti-Gal antibody activates complement and the generated chemotactic complement cleavage peptides recruit monocytes and macrophages to the injection site. The macrophages are activated by Fc/FcγR interaction with anti-Gal coated α-gal liposomes and secrete cytokines and growth factors that recruit stem cells. These stem cells and/or stem cells originating from macrophages proliferate and differentiate into Langerhans Islet cells that form the islets and secrete endogenous insulin.

Example 17

Treatment of Patients with Injuries in the Gastrointestinal Track by Injection of α-Gal Liposomes This example is aimed to study the efficacy of the compositions and methods of the present invention in recruitment of stem cells, for repair and regeneration of the gastrointestinal wall in patients with ulcer and other injuries to the gastrointestinal tract. The non-limiting example here is of ulcers in the stomach. This described treatment is applicable to any damage to the wall at any part of the gastrointestinal tract. The injured area is injected with α-gal liposomes at a concentration ranging between 0.01 and 500 mg/ml. The interaction between the injected α-gal liposomes and the anti-Gal antibody activates complement and the generated chemotactic complement cleavage peptides recruit monocytes and macrophages to the injection site. The macrophages are activated by Fc/FcγR interaction with anti-Gal coated α-gal liposomes and secrete cytokines and growth factors that recruit stem cells and promote the repair of the injured tissue. The recruited stem cells proliferate and differentiate into cells that replace the injured cells and repair the damaged gastrointestinal wall at the injection site.

Example 18

Treatment of Patients with Injuries Blood Vessels by α-Gal Liposomes

This example is aimed to study the efficacy of the compositions and methods of the present invention in recruitment of stem cells, for repair and regeneration of the blood vessel wall in patients with damaged blood vessels or in anastomoses of blood vessels by the use of α-gal liposomes. The injured blood vessel is surrounded by a device containing α-gal liposomes at a concentration ranging between 0.01 and 500 mg/ml. This device can be in the form of a gel, plasma clot or fibrin clot surrounding part or the whole injured blood vessel. Alternatively, collagen sheet or any biodegradable or non-biodegradable sheet containing the α-gal liposomes or having on its surface α-gal liposomes and which can be shaped into a tube around the injured blood vessel can be used to apply α-gal liposomes around the injured blood vessel. The interaction between the injected α-gal liposomes and the anti-Gal antibody activates complement and the generated chemotactic complement cleavage peptides recruit monocytes and macrophages to the injection site. The macrophages are activated by Fc/FcγR interaction with anti-Gal coated α-gal liposomes and secrete cytokines and growth factors that promote the repair of the injured blood vessel wall. These secreted cytokines and growth factors also recruit stem cells that proliferate and differentiate into cells that enable the regeneration of the intact blood vessel wall. Some of the recruited macrophages, which have stem cell potential, also may transdifferentiate into cells that repair the injured blood vessel.

In summary, the present invention provides numerous advantages over the prior art, including methods and compositions for the accelerated healing of wounds, repair and regeneration of injured tissues. All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in diagnostics, cell culture, and/or related fields are intended to be within the scope of the present invention.

I claim:

1. A method, comprising:
   a) providing
      i) a subject having endogenous anti-Gal antibody and an injured tissue; and
      ii) a preparation comprising a non-immunogenic composition that comprises an α-gal epitope having a terminal α-galactosyl; and
   b) applying said preparation to said injured tissue under conditions such that tissue regeneration is accelerated.

2. The method of claim 1, wherein said terminal a-galactosyl is selected from the group consisting of Galα1-3Gal, Galα1-2Gal, Galα1-6Gal, and α-galactose sugar units capable of binding anti-Gal antibodies.

3. The method of claim 1, wherein said α-gal epitope is soluble.

4. The method of claim 1, wherein said α-gal epitope is attached to a molecule selected from the group consisting of a natural glycolipid, natural glycoprotein, natural proteoglycan, natural glycopolymer, synthetic glycolipid, synthetic glycoprotein, synthetic proteoglycan, and synthetic glycopolymer.

5. The method of claim 1, wherein said preparation further comprises an injury care device selected from the group consisting of syringes, adhesive bands, compression bandages, sponges, gels, semi-permeable films, plasma clots, biodegradable sheet, non-biodegradable sheet, and fibrin clots.

6. The method of claim 1, wherein said injured tissue is selected from the group consisting of skin tissue, brain tissue, nerve tissue, eye tissue, gastrointestinal tissue, skeletal muscle tissue, heart muscle tissue, connective tissue, cartilage tissue, bone tissue, endocrine glands and vascular tissue.

7. The method of claim 1, wherein said preparation comprises α-gal liposomes.

8. The method of claim 7, wherein said α-gal liposomes further comprise anti-Gal antibodies.

9. The method of claim 7, wherein said a-gal liposomes are from 0.1 μm to 20 μm.

* * * * *